United States Patent
Savoir et al.

(10) Patent No.: US 7,589,082 B2
(45) Date of Patent: Sep. 15, 2009

(54) PHARMACEUTICAL FORMULATION FOR CONTRACEPTION AND HORMONE-REPLACEMENT THERAPY

(75) Inventors: John Claude Savoir, Coyocan (MX); Juan Angeles Uribe, Lomas de San Angel Inn (MX)

(73) Assignee: Skendi Finance Ltd, Tortola (VG)

(*) Notice: Subject to any disclaimer, the term of this patent is extended or adjusted under 35 U.S.C. 154(b) by 942 days.

(21) Appl. No.: 10/864,470

(22) Filed: Jun. 10, 2004

(65) Prior Publication Data

US 2005/0025827 A1     Feb. 3, 2005

Related U.S. Application Data

(60) Provisional application No. 60/477,939, filed on Jun. 13, 2003.

(51) Int. Cl.
A61K 31/56 (2006.01)
A61K 8/02 (2006.01)

(52) U.S. Cl. ........................ 514/170; 424/401

(58) Field of Classification Search .......... 514/170; 424/401

See application file for complete search history.

(56) References Cited

U.S. PATENT DOCUMENTS

| | | | |
|---|---|---|---|
| 3,800,038 A | 3/1974 | Rudel | |
| 4,180,560 A | 12/1979 | Katz et al. | |
| 4,218,255 A | 8/1980 | Bajpai et al. | |
| 5,211,952 A | 5/1993 | Spicer et al. | |
| 5,262,408 A | 11/1993 | Bergink | |
| 5,360,616 A | 11/1994 | Flores et al. | |
| 5,418,228 A | 5/1995 | Bennink | |
| 5,512,303 A | 4/1996 | Flores et al. | |
| 5,633,014 A | 5/1997 | Flores et al. | |
| 5,643,604 A | 7/1997 | Uribe et al. | |
| 5,762,956 A | 6/1998 | Chien et al. | |
| 5,874,063 A | 2/1999 | Briggner et al. | |
| 6,077,531 A | 6/2000 | Salin-Drouin | |
| 6,200,593 B1* | 3/2001 | Place | 424/435 |
| 6,287,693 B1* | 9/2001 | Savoir et al. | 428/402 |
| 6,528,094 B1 | 3/2003 | Savoir et al. | |
| 6,537,580 B1 | 3/2003 | Savoir et al. | |
| 6,638,536 B2 | 10/2003 | Savoir et al. | |
| 6,537,580 B1 | 3/2003 | Savoir et al. | |
| 6,638,536 B2 | 10/2003 | Savoir et al. | |

(Continued)

FOREIGN PATENT DOCUMENTS

EP    0 364 944 A1    4/1990

(Continued)

OTHER PUBLICATIONS

Search Report issued in corresponding EP Application No. 07008938.3 on Aug. 16, 2007.

(Continued)

*Primary Examiner*—San-ming Hui
(74) *Attorney, Agent, or Firm*—Buchanan Ingersoll & Rooney PC

(57) ABSTRACT

The present invention provides slow release estradiol-progesterone formulations that can be used in either contraception or hormone replacement therapies. The formulations comprise shaped particles of estradiol that is in a hemicrystalline form that exhibits especially low dissolution rates. The shaped particles comprise estradiol compounded in a 1:1 molar ratio with cholesterol, and are administered in combination with progesterone. The slow release formulations of the present invention afford the dual advantages of a low dose estradiol formulation with a low frequency administration regimen. The formulations can be parenterally administered once a month or less often.

20 Claims, 23 Drawing Sheets

U.S. PATENT DOCUMENTS

| | | |
|---|---|---|
| 6,663,895 B2 | 12/2003 | Savoir et al. |
| 6,737,081 B2 | 5/2004 | Savoir et al. |
| 2002/0168395 A1 | 11/2002 | Savoir et al. |
| 2004/0166164 A1 | 8/2004 | Savoir et al. |

FOREIGN PATENT DOCUMENTS

| | | |
|---|---|---|
| EP | 0 508 969 A | 10/1992 |
| EP | 0 508 969 A1 | 10/1992 |
| EP | 0 531 845 A1 | 3/1993 |
| GB | 1367608 | 9/1974 |
| JP | 57 099562 A | 6/1982 |
| JP | 09 557558 A | 9/1997 |
| WO | WO 91/19484 A | 12/1991 |
| WO | WO 94/22426 | 10/1994 |
| WO | WO 2004/110408 A2 | 12/2004 |

OTHER PUBLICATIONS

Search Report issued in corresponding EP Application No. 07008942.0 on Aug. 20, 2007.

Extended European Search Report issued in EP 06 02 2834.3 on Feb. 23, 2007.

* cited by examiner

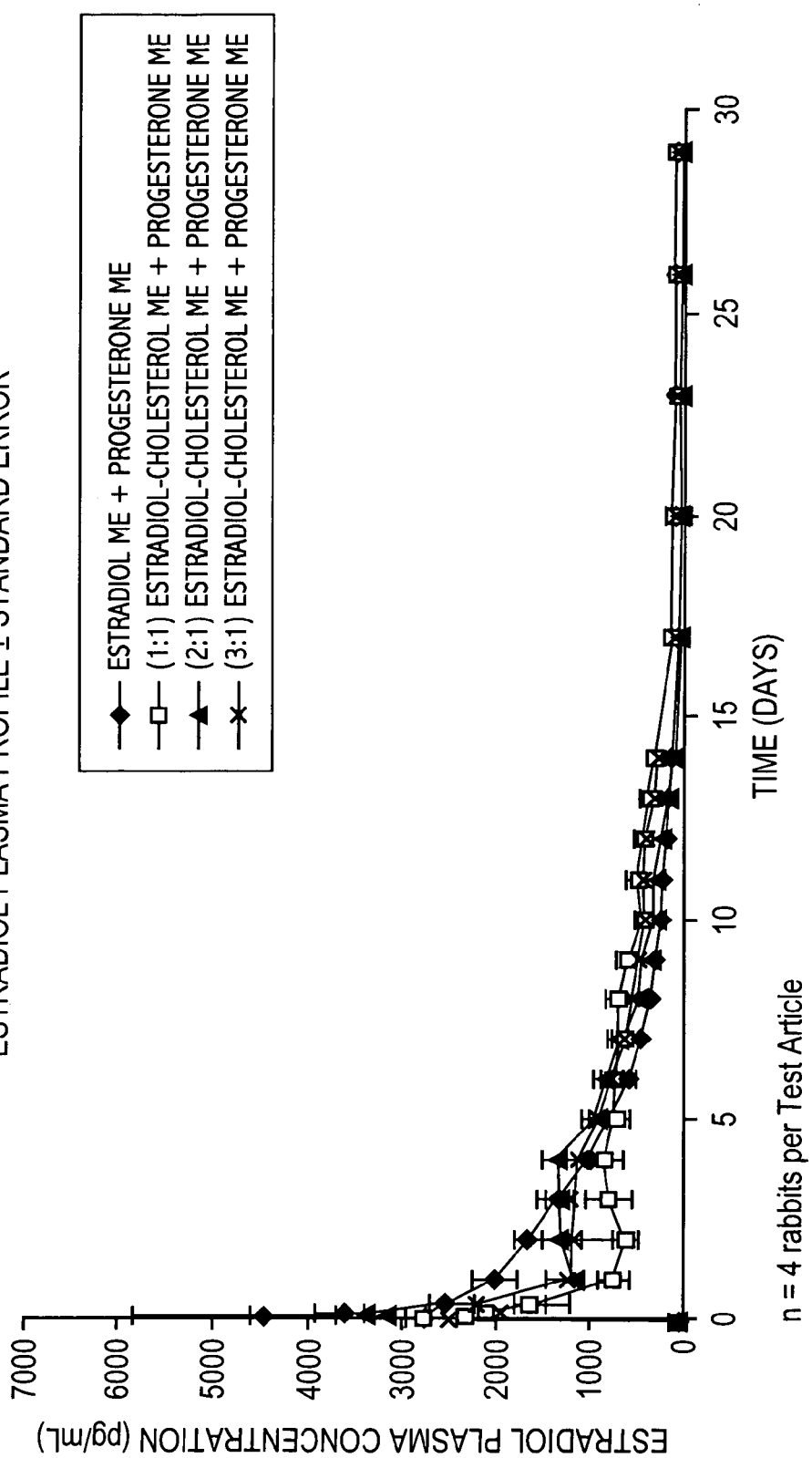

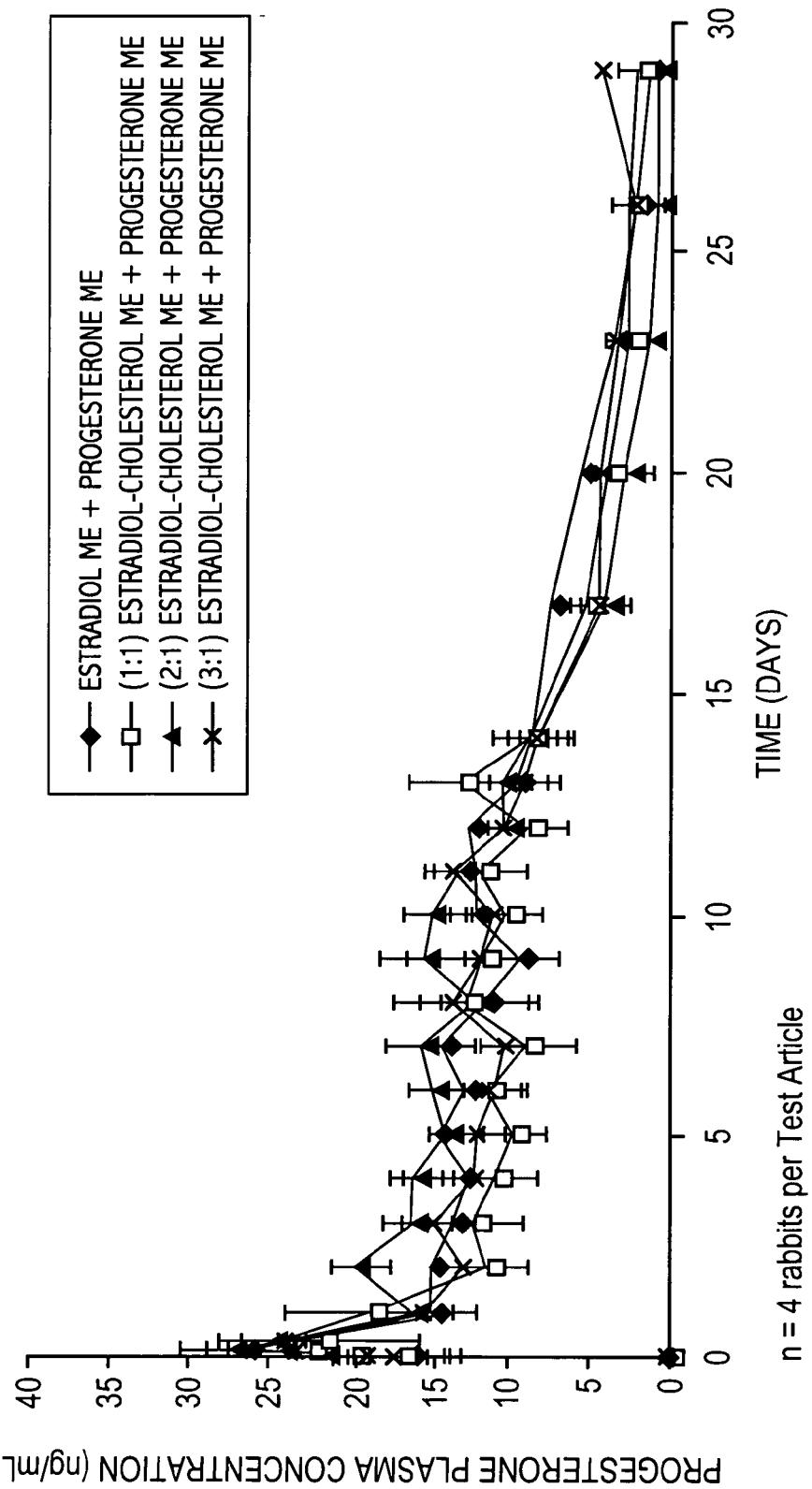

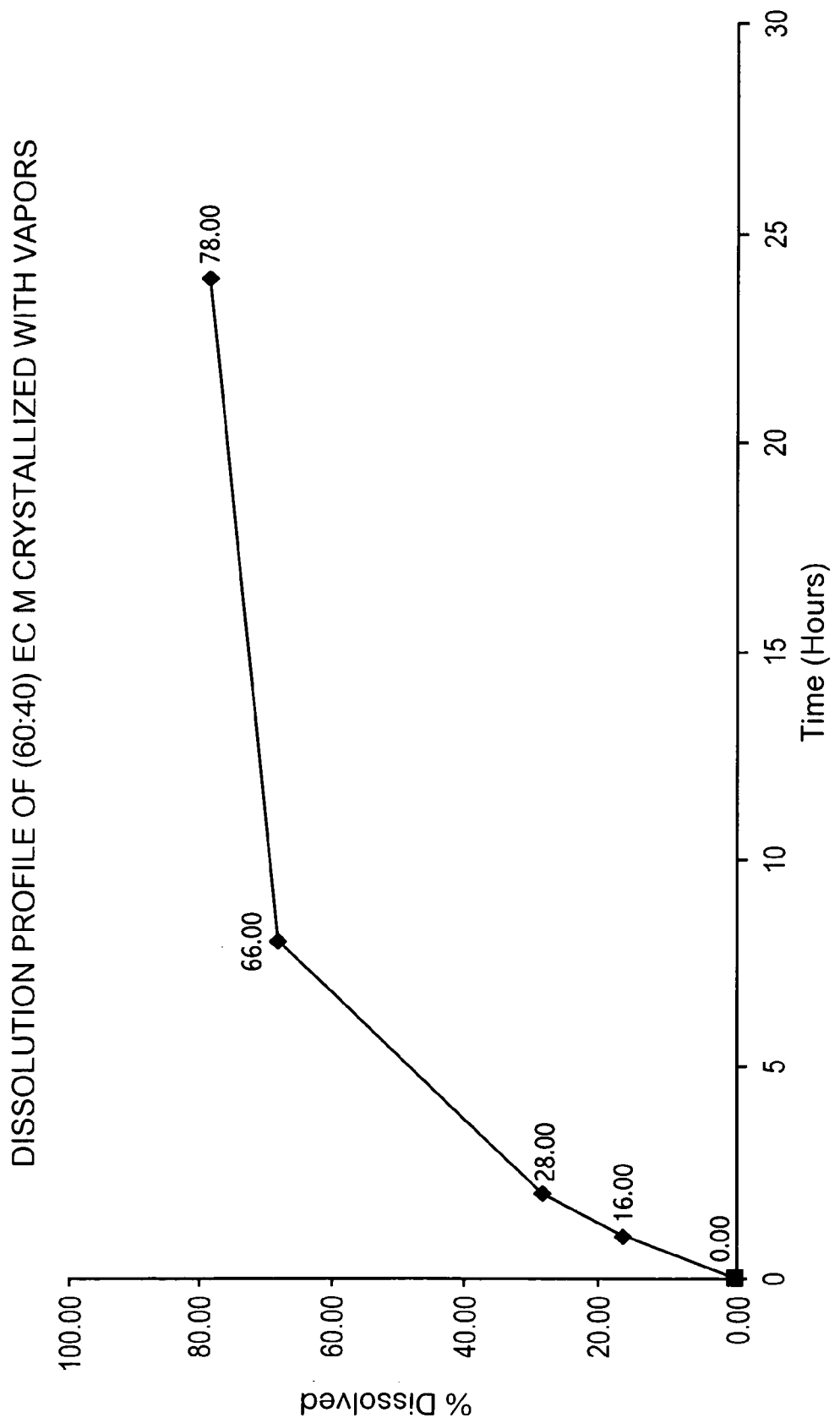

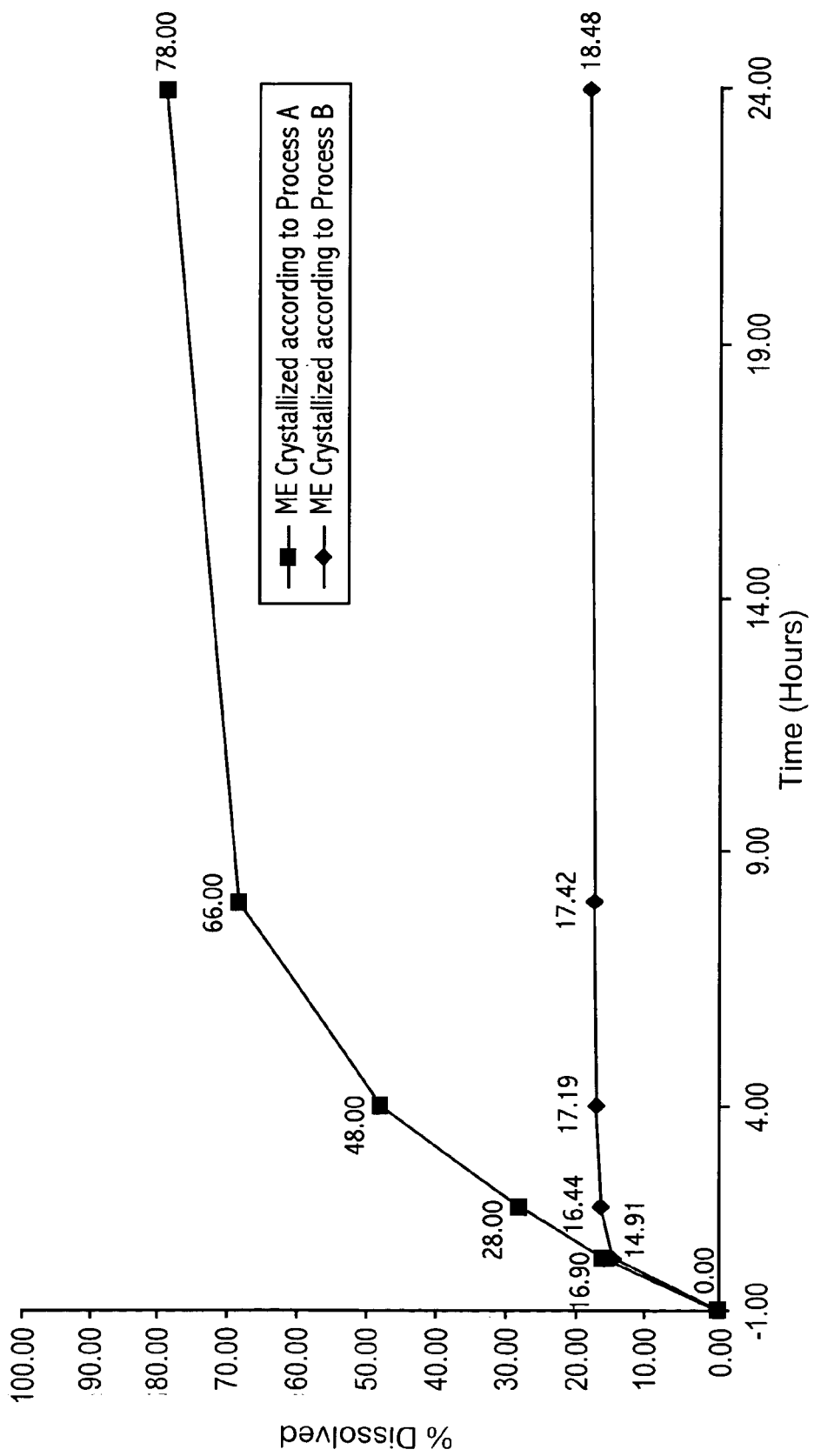

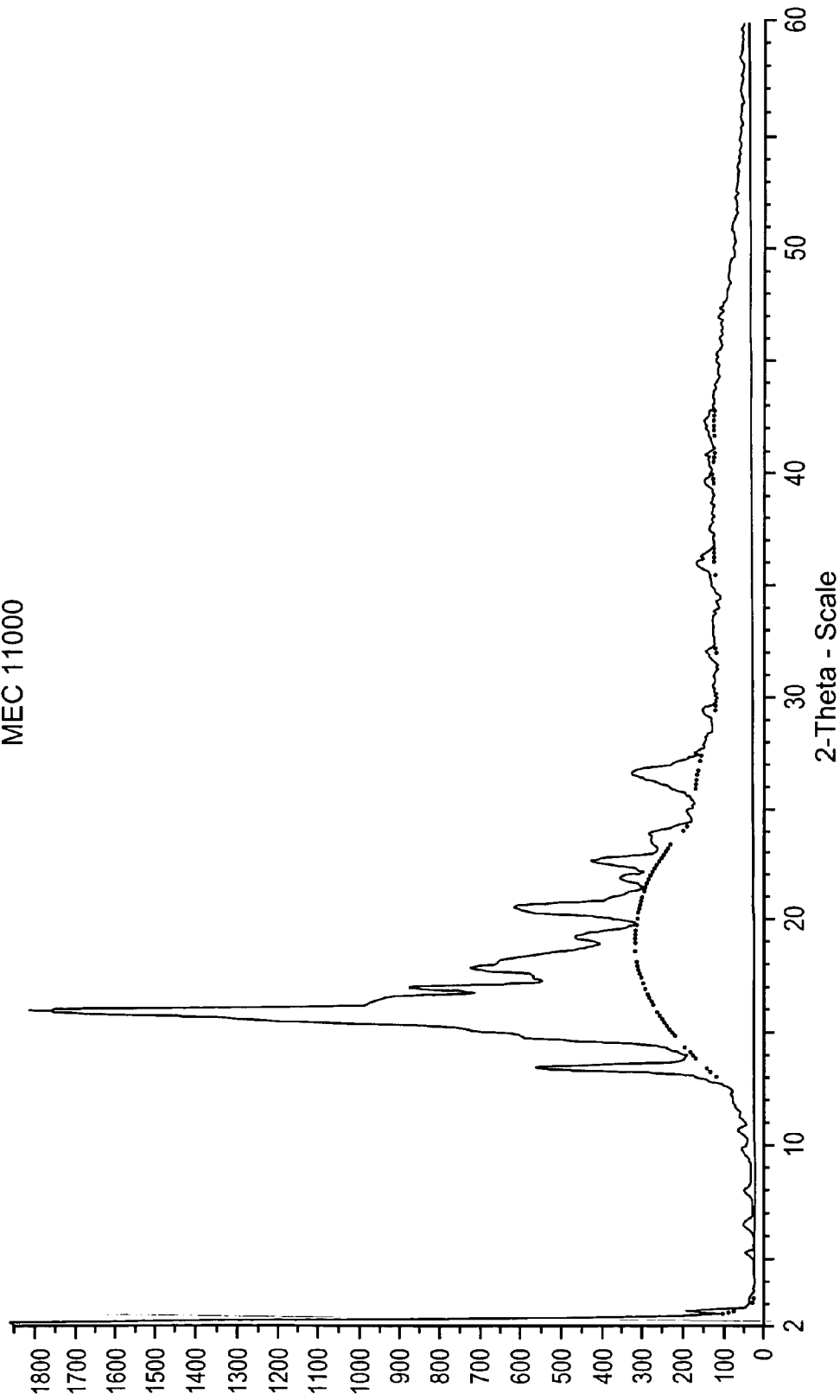

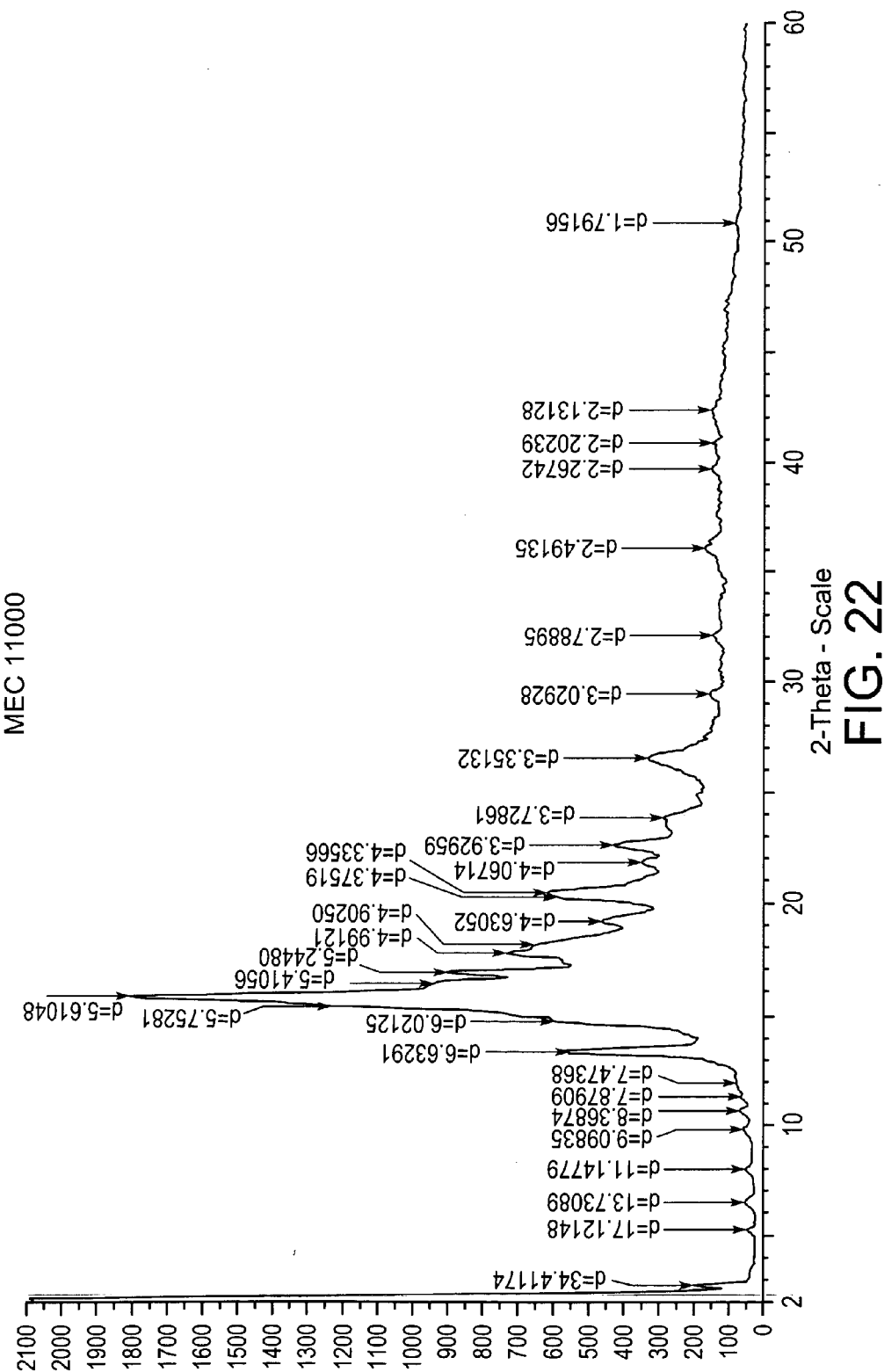

PHARMACEUTICAL FORMULATION FOR CONTRACEPTION AND HORMONE-REPLACEMENT THERAPY

The present application claims priority from provisional application Ser. No. 60/477,939, filed Jun. 13, 2003.

FIELD OF THE INVENTION

The present invention is directed to pharmaceutical formulations capable of providing simultaneous contraceptive and hormone-replacement effects. The formulations of the present invention comprise a combination of two or more natural hormones or hormone-mimetics in contraceptive-effective and hormone-replacement-effective amounts. The formulations are compounded for prolonged or delayed release facilitating administration at intervals of about four weeks or more.

BACKGROUND OF THE INVENTION

The ovarian/menstrual cycle is a complex event characterized by an estrogen-rich follicular phase and, after ovulation, a progesterone-rich luteal phase. Each phase lasts about 14 days resulting in an inter-menstrual interval of about 28 days. The endometrial tissue responds to the changes in hormonal levels.

The onset of menstruation is the beginning of a new menstrual cycle and is counted as day one. During a span of about five to seven days, the superficial layers of the endometrium, which grew and developed during the antecedent ovarian/menstrual cycle, are sloughed because demise of the corpus luteum in the non-fertile menstrual cycle is associated with the loss of progesterone secretion. Ovarian follicular maturation occurs progressively resulting in a rise in the circulating levels of estrogen, which in turn leads to new endometrial proliferation.

The dominant ovarian follicle undergoes ovulation at mid-cycle, generally between menstrual cycle days 12 to 16 and is converted from a predominantly estrogen source to a predominantly progesterone source (the corpus luteum). The increasing level of progesterone in the blood converts the proliferative endometrium to a secretory phase in which the tissue proliferation has promptly abated, leading to the formation of endometrial glands or organs. When the ovulated oocyte is viably fertilized and continues its progressive embryonic cleavage, the secretory endometrium and the conceptus can interact to bring about implantation, beginning about six to eight days after fertilization.

If an ongoing pregnancy is to be established by implantation, the embryo will attach and burrow into the secretory endometrium and begin to produce human chorionic gonadotropin (HCG). The HCG in turn stimulates extended corpus luteum function, i.e., the progesterone function remains elevated, and menses does not occur in the fertile menstrual cycle. Pregnancy is then established.

In the non-fertile menstrual cycle, the waning level of progesterone in the blood causes the endometrial tissue to be sloughed. This starts a subsequent menstrual cycle.

Because endometrial proliferation serves to prepare the uterus for an impending pregnancy, manipulation of hormones for the uterine environment can provide contraception. For example, estrogens are known to decrease follicle stimulating hormone secretion by feedback inhibition. Under certain circumstances, estrogens can also inhibit luteinizing hormone secretion, once again by negative feedback. Under normal circumstances the spike of circulating estrogen found prior to ovulation induces the surge of gonadotropic hormones that occurs just prior to and resulting in ovulation. High doses of estrogen can prevent conception probably due to interference with implantation.

Progestins can also provide contraception. Endogenous progesterone is responsible for the progestational changes in the endometrium and the cyclic changes of cells and tissue in the cervix and the vagina. Administration of progestin makes the cervical mucus thick, tenacious and cellular, which is believed to impede spermatozoal transport. Administration of progestin also inhibits luteinizing hormone secretion and blocks ovulation in humans.

There are a number of contraceptive formulations currently on the market that can be classified readily into several general types. The first of these are known as monophasic formulations. Monophasic formulations contain a constant amount of estrogen and progestin. Nuisance side effects with monophasic formulation pills depend on the balance between the estrogen and progestin component of the pill. For example, with a relatively dominant progestin pill, the formulation will, over time, result in a depletion of both estrogen and progestin receptors. The result, which might be expected, is an under stimulated or atrophic endometrium, which may eventually cause either un-pill amenorrhea or breakthrough bleeding or spotting due to poor epithelialization. On the other hand, with a relatively dominant estrogenic preparation, it is possible that prolonged use could result in endometrial growth with the development of unsupported fragile stroma and subsequent spotting or breakthrough bleeding.

New formulations known as triphasics have varying levels of estrogen and progestin; in most cases consisting of relatively constant levels of estrogen with a step-wise increase in progestin throughout the cycle. This pattern of estrogen and progestin administration results in a relatively dominant estrogenic formulation at the beginning of the package with increasing progestigenic activity toward the end of the package. Endometrial stability may be better with these pills since the estrogenic activity at the beginning of the package induces both estrogen and progestin receptors making the endometrium sensitive to the increased levels of progestin towards the end of the package. The progestin activity produces denser, more stable endometrial stroma although the relatively long duration of progestin exposure, toward the end of the package, may still lead to decreased estrogen and progestin receptors and activity.

A significant problem with this type of formulation is the low dose of steroids at the beginning of the package, which makes these pills vulnerable to drug interactions, or missed pills, which may lead to breakthrough ovulation. The beginning of the package is the critical time in terms of breakthrough ovulation since the user has just completed a seven day drug-free interval during which follicular development may begin. Even if pregnancy does not occur, breakthrough ovulation can lead to poor cycle control.

17-β-estradiol ($E_2$) is the most potent natural estrogen found in human beings and is the major secretory product of the ovary. It is readily oxidized in the body to estrone E, which in turn can be hydrated to estriol. These transformations take place mainly in the liver, where there is free interconversion between $E_1$ and estradiol. All three of these natural estrogens are excreted in the urine as glucuronides and sulfates, along with a host of related, minor products in water-soluble complexes. It is widely known that, following oral administration of micronized E2, the incremental circulation of estrogen is principally the less active species E1, which reaches a peak concentration many times greater than that of E2. The conversion of E2 to E1 and subsequently to other metabolites takes place during absorption from the intestine and passage through the liver. This extensive metabolism greatly limits the oral effectiveness of the natural estrogens and their esters. Indeed, because of their limited oral efficacy, E2 and its esters are generally administered by intramuscular injections.

Progesterone (P4) is the active natural progestin, which occurs in the corpus luteum, placenta and adrenal cortex. Like E2, P4 is also ineffective by oral administration because of its rapid metabolism in the intestinal epithelium and in the liver, and is therefore only administered intramuscularly.

Because of their limited oral effectiveness, workers in the art consider these natural female sex hormones as undesirable in the formulation of oral contraceptives. Instead, workers have focused on the fabrication and administration of synthetic estrogens and progestins for contraceptive purposes. The use of synthetic derivatives has also replaced natural substances in the treatment of menopause, threatened abortion, etc. However, these synthetic derivatives are more likely to cause toxic side effects than are the relatively safe endogenous hormones.

While chemical modifications of natural hormones exhibit enhanced oral activity, they also can cause a variety of undesirable side effects. For example, synthetic derivatives of natural hormones are known to have an adverse stimulating effect on the protein synthesis of the liver (possibly promoting thrombosis) and exhibit a diabetogenic effect, in contrast to natural sex hormones.

Synthetic estrogen, for example, is rapidly resorbed in the stomach and intestinal track. Because it is easily metabolized, it is rapidly absorbed in the mucus membrane of the small intestine and/or undergoes rapid chemical changes. Consequently, large individual differences in bio-availability can result. Further, synthetic estradiols can lead to an undesirable accumulation of certain zenobiotics and are known to exhibit carcinogenic properties.

Synthetic progestins are also known to exhibit undesirable side effects including, for example, masculinization and adverse effects on cholesterol levels, triglyceride levels and high-density lipoprotein levels. Synthetic progestins can also cause fluid retention and depression.

An additional undesirable side effect that can affect subjects undergoing synthetic hormonal contraceptive treatment is the reduction/cessation of natural hormone production. Many subjects also experience an undesirable hormone imbalance resulting from the cessation of ovulation due to the contraceptive effect of administered synthetic hormones.

Accordingly, there is an urgent need for a pharmaceutical formulation that includes endogenous hormones that can be administered in amounts effective to provide not only a contraceptive effect but also a hormone-replacement effect.

SUMMARY OF THE INVENTION

The present invention provides a means for administering the natural hormones with a prolonged life in the organism by means of a depot system. The administration of the natural hormones precipitates the negative feedback effect while providing replacement of the inhibited endogenous hormones.

The present invention provides a pharmaceutical formulation for simultaneous contraceptive and hormone-replacement purposes comprising a contraceptive-effective and hormone-replacement effective amount of a combination of natural hormones or hormone-mimetics. Preferably, the formulation comprises at least one estrogen and at least one progestin. Still more preferably, the formulation comprises the naturally occurring hormones 17-β-estradiol (E2) and progesterone (P4).

By administering effective amounts of E2 and P4, the formulations of the present invention provide effective and reliable contraception without the undesirable side effects commonly associated with contraceptives formulated with orally active synthetic hormones. Additionally, because the pharmaceutical formulations are compounded to produce a prolonged dissolution profile, the hormones have high mean residence times and avoid the shortcomings of the traditional short half-life of the natural hormones. Among other things, the formulations of the present invention are prepared in accordance with methods disclosed in U.S. Pat. No. 5,360, 616 and crystallized according to methods disclosed in U.S. Pat. No. 6,528,094 B1, both of which are incorporated herein by reference.

The formulations of the present invention provide effective hormone-replacement benefits. Because the formulations are compounded with naturally occurring hormones, administration of those formulations serves to restore or supplement the naturally occurring hormones otherwise produced in a female mammal of reproductive age. Conventional contraceptives comprised of orally-active, synthetic hormones do not provide such hormone-replacement benefits.

The estrogen and progestin agents of the formulations of the instant invention are present in the formulation in a contraceptive-effective and hormone-replacement-effective amount. On a unit dose basis, formulations of the present invention will comprise about 5 to about 15 mg of 17-β-estradiol and/or about 200 to about 500 mg of progesterone. Particularly preferred embodiments are formulations that comprise about 9 mg of 17-β-estradiol and about 400 mg of progesterone per unit dose. Thus, the term "contraceptive-effective and hormone-replacement effective amount" of 17-β-estradiol and progesterone, when referring to a mammal, particularly a female human, is meant to refer to a formulation comprising 17-β-estradiol and progesterone in a weight ratio of about 1:40. Preferably, the weight ratio is about 9:400. The term "unit dose" refers to an amount sufficient to effect both contraception and hormone-replacement therapy in one subject throughout at least one complete menstrual cycle.

In one embodiment, the pharmaceutical formulation comprises a plurality of microspheres that comprise at least one of 17-β-estradiol and progesterone, and the microspheres are suspended in an aqueous vehicle for administration. (As used herein, the term microspheres includes microparticles, microcapsules, liposomes, and the like.) Preferably, the estradiol and progesterone in the microsphere are in crystalline form.

In accordance with a further aspect of the invention, the pharmaceutical formulation comprises an aqueous preparation comprising microspheres of an estrogen and/or a progestin. The microspheres are preferably about 25 μm to about 105 μm in diameter; more preferably about 35 μm to about 75 μm. The microspheres are preferably compounded with other agents, carriers, and excipients such that the formulation is suitable for parenteral administration by hypodermic syringe.

According to a further aspect of the present invention, a simultaneous contraceptive and hormone-replacement effect can be achieved by administering to a subject a pharmaceutical formulation comprising a contraceptive-effective and hormone-replacement-effective amount of 17-β-estradiol and progesterone. The subject of such administration is preferably a female mammal of reproductive years, also referred to herein as a "fertile female."

In accordance with another aspect of the invention, a method for simultaneous contraception and hormone-replacement effects comprises administering to a subject a pharmaceutical formulation comprising microspheres of at least one of 17-β-estradiol and progesterone. Preferably, the formulation is a dispersion or suspension of said microspheres in a liquid vehicle. The 17-β-estradiol and progesterone are present in the formulation in a contraceptive-effective and hormone-replacement-effective amount. In the case of female humans, the effective amount of 17-β-estradiol is about 9 mg and the effective amount of progesterone is about 400 mg.

In accordance with a further aspect of the invention, a method of simultaneous contraception and hormone-replacement effect includes parenteral administration of an estrogen/progestin pharmaceutical formulation into a subject. Preferably, the formulation is administered by intramuscular injection. The pharmaceutical formulations of the present invention are delayed or prolonged release formulations that can be effectively administered at intervals of about four weeks without loss of the contraceptive or hormone-replacement effect during the intervening period.

The formulations of the present invention can be compounded into a variety of forms for storage, shipment, or administration. The formulations can be compounded as microspheres, powders, mixtures, suspensions, or gels. When the estrogen/progestin agents of the instant formulations are compounded as dispersions of microspheres in an aqueous vehicle for parenteral administration, the particle size is preferably about 25 μm to about 105 μm; and more preferably about 35 μm to about 75 μm.

A further aspect of the present invention provides a kit comprising a pharmaceutical formulation comprising a contraceptive and a hormone-replacement effective amount of 17-β-estradiol and progesterone. Preferably, the kit comprises a formulation comprising microspheres, wherein the microspheres comprise at least one of 17-β-estradiol and progesterone and wherein the formulation comprises about 9 mg of 17-β-estradiol and about 400 mg of progesterone.

The present invention, through the use of contraceptive-effective and hormone-replacement effective amounts of 17-β-estradiol and progesterone, realizes an important advantage in that it can substantially minimize or eliminate the undesirable side effects commonly associated with conventional, synthetic hormone-containing contraceptive formulations. Additionally, through the use of effective amounts of these endogenous hormones, the present invention realizes another important advantage in that it can provide subjects with natural hormones at levels equivalent to the average natural monthly production, thereby avoiding undesirable hormone imbalances.

BRIEF DESCRIPTION OF THE DRAWINGS

FIG. 1: Plot of estradiol mean plasma profile, arithmetic scale.

FIG. 2: Plot of progesterone plasma profile, arithmetic scale.

FIG. 4: The dissolution profile of (60:40) estradiol-cholesterol microspheres after solid state crystallization according to the method of U.S. Pat. No. 6,528,094 B1.

FIG. 5: Comparative dissolution profiles of (1:1) estradiol-cholesterol microspheres prepared by Crystallization Process A (Example 2) and Crystallization Process B (Example 3).

FIG. 21: X-ray diffractogram of microspheres of estradiol-cholesterol (1:1) made according to Process C.

FIG. 22: X-ray diffractogram of microspheres of estradiol-cholesterol (1:1) made according to Process C.

DETAILED DESCRIPTION OF THE PREFERRED EMBODIMENTS

Figure 3A:
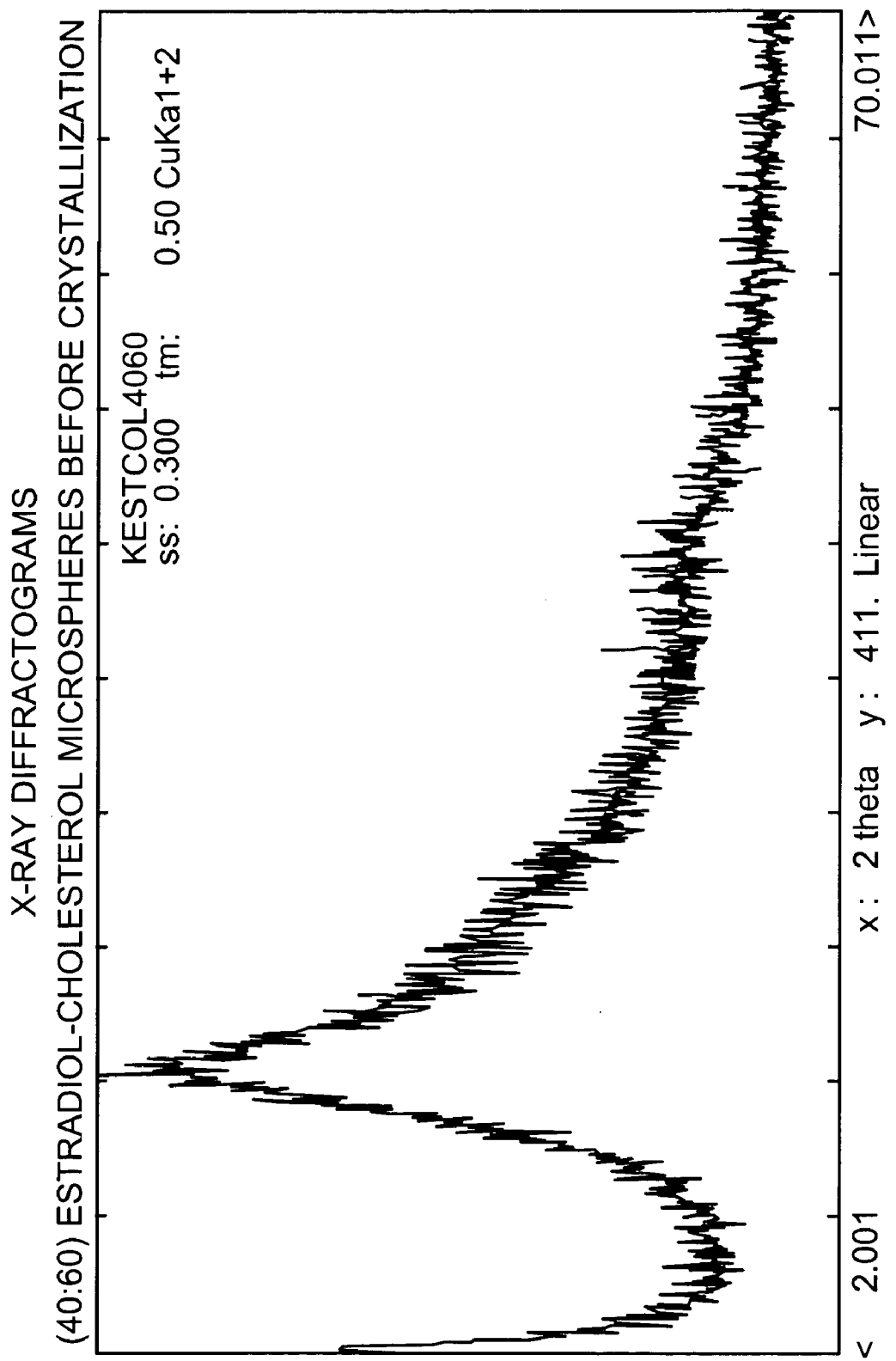
FIG. 3A: An X-ray diffractogram of (40:60) estradiol-cholesterol microspheres before crystallization.

In the present invention, contraceptive-effective and hormone-effective amounts of 17-β-estradiol and progesterone are administered to a subject in a controlled manner to substantially minimize and/or eliminate undesirable side effects commonly associated with synthetic hormone contraceptive therapies. Additionally, the present invention provides these natural hormones at levels equivalent to their average natural monthly production.

The term "17-β-estradiol," as used herein, encompasses any pharmaceutically-acceptable, estrogenically-active form of 17-β-estradiol, i.e., estra-1,3,5(10)-triene-3,17-β-diol itself, which has the formula:

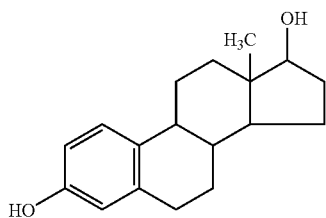

or one of its esters. 17-β-estradiol can be obtained from natural sources or made synthetically. Suitable esters of 17-β-estradiol, for purposes of the present invention, include, for example, 3-monoesters such as estradiol benzoate and estradiol 3-acetate; 17-monoesters such as estradiol cyponate, estradiol 17-propionate, estradiol 17-acetate, estradiol 17-heptanoate (estradiol enanthate), estradiol 17-undecanoate (estradiol undecylate) and estradiol 17-val-erate; and 3,17-diesters such as estradiol dipropionate and estradiol diacetate, and the like, and combinations thereof.

The term "progesterone," as used herein, refers to pregn-4-ene-3,20-dione, i.e., the compound of the formula:

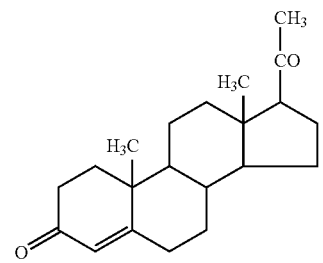

and is intended to include progesterone derived from natural sources as well as that made synthetically.

In preferred embodiments of the present invention, the pharmaceutical formulations comprise aqueous suspensions of microspheres comprising an estrogen (e.g., 17-β-estradiol (E2)) and a progestin (e.g., progesterone (P4)) in a contraceptive-effective and hormone-replacement-effective amount. The individual microspheres might contain one or both of the estrogen or progestin. Regardless of whether or not E2 and P4 are both present in each microsphere, each is present in the formulation in an amount effective to provide a contraceptive and a hormone-replacement effect. Thus, even if E2 and P4 are not present together in a single microsphere, they are each present in the formulation in effective amounts.

Additionally, the microspheres of such embodiments can comprise additional endogenous steroids such as cholesterol.

The additional endogenous steroids are preferably inert relative to the estrogen/progestin agents and have substantially reduced solubility in biological fluids such as blood. When so formulated, the cholesterol/estrogen/progestin microspheres are compounded in such a way that the estrogen/progestin agents are uniformly distributed throughout the relatively inert steroid such that the dissolution of those agents is retarded but nonetheless continuous and substantially steady. Preferably, the inert steroid, as well as the estrogen and progestin, are in crystalline form within the microsphere. As discussed more fully below, the substantially steady rate of dissolution of the active agents thus facilitates a controlled release of the active agents over an extended period. Preferably, the extended period is at least one complete menstrual cycle, and in the case of a female human it is at least about 4 weeks.

In embodiments of the invention, the contraceptive-effective and hormone replacement-effective amounts of E2 and P4 are amounts that are suitable for providing a simultaneous contraceptive and hormone-replacement effect. In particular, with respect to the contraceptive effect, the effective amount of E2 and P4 is an amount that is sufficient to act on the hypothalamus and the pituitary of the subject being treated to inhibit the liberation of gonadotrophic hormones necessary for maintaining normal ovarian function.

In addition, the hormone-replacement-effective amount of E2 and P4 is an amount sufficient to substantially replace the natural supply of these hormones whose endogenous production is reduced and/or eliminated with the cessation of ovulation.

In preferred embodiments of the invention, the contraceptive-effective and hormone-replacement-effective amounts of E2 and P4 are those suitable for achieving the desired effect in a female human, and, on a unit dose basis are about 5 mg to about 15 mg estradiol and about 300 mg to about 500 mg progesterone. More preferred embodiments comprise about 9 mg 17-β-estradiol and about 400 mg progesterone.

The formulation of the present invention comprises hormone-containing microspheres to provide controlled, predictable and reproducible administration of the hormones contained therein. Various physicochemical characteristics of the microspheres are important to achieving controlled release of the hormones. In particular, solubility, size and polymorphic composition of the microspheres have a substantial effect on the rate of release. For instance, the greater the diameter of the microsphere, the longer it takes for the hormone level to reach undetectable values. In the present invention, the diameter of the microspheres is preferably about 25 μm to about 125 μm; more preferably about 35 μm to about 105 μm; and most preferably about 35 μm to about 75 μm.

As the natural hormones E2 and P4 are known to metabolically degrade when administered orally, the formulation of the present invention is preferably administered to subjects by parenteral administration, particularly intramuscular injection. In methods of the present invention, the goal is to provide a contraceptive effect while simultaneously providing a hormone-replacement effect by supplying natural levels of E2 and P4. Further, the pharmaceutical formulations and methods of the present invention promote the establishment of healthy monthly menstrual cycles of about 28 days±3 days. In preferred embodiments, the formulations of the present invention are administered to a subject by injection on a monthly basis using a suitable means of injection such as, for example, an 18 or 20 gauge hypodermic needle.

Preferred pharmaceutical formulations of the instant invention comprise contraceptive-effective and hormone-replacement-effective amounts of an estrogen and a progestin compounded in a prolonged or delayed release formulation. Such delayed release formulations can include the estrogen and progestin compounded with a carrier, excipient, or binder having reduced solubility in the biological fluids at the site of administration. For example, such delayed release formulations might comprise microspheres wherein the estrogen and progestin are compounded with a naturally occurring steroid such as cholesterol in a microsphere. Cholesterol has substantially less solubility in biological fluids such as blood as compared to estrogens and progestins, and thereby diminishes the dissolution of those active agents, and thereby delays the release of those active agents into the bloodstream. Additional information that might be instructive in the preparation of such delayed release microsphere formulations is found in U.S. Pat. Nos. 5,360,616; 5,512,303; 5,633,014; 5,643,604; and 6,287,693, each of which is hereby incorporated by reference.

In at least one preferred embodiment, a delayed-release formulation of the present invention is prepared by mixing the estrogen and progestin thoroughly and uniformly throughout a cholesterol carrier. The estrogen/progestin/cholesterol mixture can be melt congealed and/or extruded or otherwise processed into a plurality of particles of desired size and shape, and subjected to a solid state crystallization as disclosed in U.S. Pat. No. 6,287,693. The '693 patent discloses a solid state crystallization process whereby a composition of mixed morphologies is formed into particles of desired size and shape, and subsequently crystallized to the most stable polymorph of each of the respective constituents without loss of the particle's size/shape characteristics by exposing the particles to an environment having a high atmospheric concentration of one or more solvents. The resulting shaped crystalline particles are storage stable, that is they can be packaged and stored as a dry solid or powder or as a suspension in an aqueous vehicle for extended periods (e.g., at least about one month) without loss of the desired size/shape characteristics. Because the solid state crystallization process affords high purity and stability, the particles of the present invention can be fabricated with or without additional excipients, buffers, stabilizers, preservatives, and biocides.

The ability to fabricate particles of desired size and shape is particularly advantageous as it provides a means for ensuring consistent or even uniform particle size and shape, which in turn ensures ease of administration (e.g., via hypodermic syringe), and controlled and predictable dissolution and release of the active agent(s). In particularly preferred embodiments, the particles are microspheres.

Thus, another preferred embodiment of the invention comprises a delayed release formulation comprising a plurality of microspheres in suspension in an aqueous vehicle, the microspheres comprising 17-β-estradiol, progesterone, and cholesterol, and wherein the formulation comprises 17-β-estradiol and progesterone in a ratio of about 1:40 by weight.

The formulations of the present invention may be administered by any conventional route of administration. The preferred route of administration is parenteral administration, and a more preferred route is by intramuscular (IM) injection. When administered by parenteral administration, it is preferred that the formulation be compounded as a fluid, whether in solution or as a mixture such as a suspension. Preferably, the formulation comprises the microspheres discussed above as a suspension in an aqueous vehicle.

Optionally, the formulation can be compounded as a powder for subsequent admixture with a carrier and administration. In such embodiments, the pharmaceutical formulation can be packaged and commercialized as part of a kit. Such a kit might comprise unit or multiple doses of: (1) a powder comprising the active agents in combination with excipients, additives, buffers, preservatives, and the like; (2) unit or multiple dose quantities of a fluid carrier, optionally comprising buffers, preservatives, and/or biocides; and (3) an injection device such as a hypodermic syringe, preferably about an 18 or 20 gauge syringe.

Still another option for the administration of the formulations of the present invention is transdermal delivery. Transdermal delivery of drugs can be effected by various means including injection of a powder as by a biolistic method wherein particles are accelerated by a gas or other means to pass through the skin. An example of such an approach is described in U.S. Pat. No. 6,168,587, entitled "Needleless syringe using supersonic gas flow for particle delivery"; and U.S. Pat. No. 6,475,181, entitled Drug Particle Delivery", both of which are incorporated herein by reference.

Similarly transdermal delivery can be achieved more passively as by adhesive patches applied to the skin for extended periods. Such patches are described in, e.g., U.S. Pat. No. 6,149,935, entitled "Solid matrix system for transdermal drug delivery", incorporated herein by reference.

The pharmaceutical formulations of the present invention can be effectively administered to any mammalian organism such as a primate, canine, feline, ovine, equine, porcine, bovine, or murine organism. Preferably, the subject is a primate organism, and still more preferably is a female human. It will be understood that the particular estrogen and progestin utilized in formulations for different mammals may vary, as will the quantities.

The microsphere-containing formulation of the present invention can be prepared using any suitable method. In one preferred embodiment, the microspheres are prepared by heating E2 and/or P4 and then rapidly cooling so that the microspheres become sufficiently crystallized. Subsequent to crystallization, the capsules can be collected by filtration on a particle-size basis.

Generally, the larger-sized microspheres decrease the maximum concentration of the hormones and the time required to reach that concentration. Additionally, larger-sized microspheres increase the hormone absorption half-life.

According to a further aspect of the invention, a kit is provided for use in contraceptive/hormone-replacement therapy. The kit can comprise a pharmaceutical formulation according to the invention, which comprises a contraceptive-effective and a hormone-replacement-effective amount of 17-β-estradiol and progesterone. The kit can further comprise one or more additional components such as a sterile ampule comprising an aqueous vehicle for reconstituting the formulation into a homogeneous suspension, if the formulation is provided in microspheres in sterile powder form. Further, the kit can include means for administering the formulation such as, for example, syringes with 18 and/or 20 gauge needles for intramuscular injection.

It is contemplated that the compositions of the present invention can be formulated and administered in accordance with the following protocol. A microsphere formulation comprising 9 mg of E2/400 mg P4 is prepared as a sterile powder wherein the microspheres range in size from about 35 μm to about 75 μm, preferably about 39 μm to about 52 μm. In certain preferred embodiments, the powder is packaged dry in unit dose syringes. Preferred are syringes of about 18 or 20 gauge needles for intramuscular injection. The syringes are preferably packaged in air-tight, sterile packaging, and stored under ambient conditions at about 15° C. to about 30° C.

The pre-packaged powder formulation can be suspended in an aqueous vehicle. In a preferred embodiment, the aqueous vehicle is taken from a sterile ampule containing 3.0 ml of an aqueous vehicle. A preferred aqueous vehicle used to suspend the microspheres is composed of:

| | |
|---|---|
| Methyl paraben NF | 4.11 mg |
| Propyl paraben NF | 0.45 mg |
| Mannitol NF | 144 mg |
| Sodium Carboxymethylcellulose, USP, low viscosity | 2.25 mg |
| Polysorbate 80 NF | 0.60 mg |
| Water for Injection USP | 3.00 mg |

One of ordinary skill in the art will understand that the composition and relative concentrations of such an aqueous vehicle are not critical to the present invention, and thus both can be varied without substantially altering or diminishing the advantages or utility of the present invention.

Reconstitution can be effected by vigorous agitation until a homogenous suspension is obtained. The resulting suspension is preferably administered by deep intramuscular injection, e.g., in the gluteal region. The first dose should be given in the first five days from the start of the last menstruation. Subsequent doses are to be administered on a schedule of every 28±3 days. For ease and comfort, the subsequent doses can be administered in alternating gluteal regions.

Alternatively, the progesterone/estradiol pharmaceutical formulations of the present invention can be compounded to produce a slow release estradiol formulation.

A pharmaceutical formulation comprising microspheres of progesterone and microspheres of estradiol and cholesterol produced a reliable contraceptive effect. See Example 1, Test article B, below. A recognized shortcoming of estradiol-containing parenteral contraceptive formulations is its high solubility in aqueous solutions. Estradiol-containing microspheres can be formulated by post-fabrication treatment or tempering of the microspheres. That is, the microspheres are first formed into the desired size and shape, subjected to a treatment or tempering step in a controlled atmosphere, and then dried and/or recovered. Depending on the treatment, the EC microspheres have an estradiol dissolution rate in aqueous solution over 24 hours of about 20% or less, and preferably about 15% or less. More preferred embodiments afford dissolution rates of about 10% or less; and still more preferred are those having an estradiol dissolution rate of about 6% or less.

The estradiol dissolution rate (EDR) is a measure of the quantity of estradiol dissolved in an aqueous solution of 0.3% w/v polyoxyethylenesorbitan monooleate (Tween 80®) in USP purified water for 24 hours at 37° C. and standard pressure.

The production of particles having low EDR facilitates the preparation of a pharmaceutical formulation for hormone replacement therapy (HRT) containing very low concentration of estradiol. Such low estradiol-concentration compositions are well suited to patients in need of HRT during the first five years of menopause. Further, formulations having low EDR facilitate a treatment regimen involving fewer, or lower frequency, courses of administration. It is contemplated that the formulations of this invention can be administered as infrequently as monthly or every other month.

X-ray diffraction studies of the particles demonstrating such low rates of estradiol dissolution suggest that the particles are molecular aggregates with a hemicrystalline composition comprising both an amorphous and a crystalline component. Low EDR compositions are those wherein the estradiol consists of about 45% to about 65% amorphous component, and about 35% to about 55% crystalline component. Preferably, the particles are about 50-60% amorphous component and about 40-50% crystalline component. More preferably, the particles are about 55% amorphous component and about 45% crystalline component. These low EDR compositions are preferably formulated from a mixture of a 1:1 molar ratio of estradiol:cholesterol.

Without wishing to be bound by any theory or scientific principle, applicants believe that the reduced solubility and lower dissolution profile is attributable to the orientation of the amorphous component and the crystalline component within the molecular aggregate or molecular composite. That is, it is contemplated that the exterior surface of the particle is comprised predominantly of the amorphous component such that the molecules of estradiol orient a predominantly hydrophobic portion of the molecule toward the solvent thus making the particles substantially insoluble in water.

Slow release estradiol particles can be formulated by compounding estradiol and cholesterol in a 1:1 molar ratio, fabricating the composition into particles of the desired size and shape, and subjecting them to a solvent-saturated atmosphere for an extended period at elevated temperature, and subsequently, drying the particles at elevated temperature. In one embodiment, the fabricated particles are exposed to an atmosphere of low relative humidity (RH) for about 12 hours or more prior to exposure to the solvent-saturated atmosphere. Preferably, the particles are formulated as microspheres.

Microspheres having an EDR of about 15% or less can be formulated by: creating particles consisting essentially of a 1:1 molar ratio of estradiol and cholesterol wherein either or both are in an amorphous or polymorphous form; exposing the particles to an atmosphere of about 25% relative humidity (RH) or less for at least about 12 hours; exposing the particles to an atmosphere saturated with acetone and water for at least about 48 hours at about 50° to about 65° C.; drying the particles at about 35° to about 50° C. for about 24 hours or more; and recovering said particles; wherein the EDR from the recovered particles is less than about 15% (by weight) over 24 hours.

More preferably, the method involves creating particles consisting essentially of estradiol and cholesterol wherein either or both are in an amorphous or polymorphous form; exposing said particles to an atmosphere of low RH for about 24 hours; exposing the particles to an atmosphere saturated with acetone and water for about 72 hours at about 60° C.; drying the particles at about 45° C. for about 42 hours; and recovering said particles; wherein the estradiol dissolution rate from the recovered particles in aqueous solution is less than about 6% (by weight) over 24 hours.

The relative concentrations of acetone and water saturating the atmosphere are about 65 mole % to about 80 mole %, and about 20 mole % to about 35 mole %, respectively. Preferably, the relative concentrations are about 70 mole % to about 75 mole % acetone; and about 25 mole % to about 30 mole %, water. Most preferably, the concentrations of the two components are about 72 mole % acetone to about 28 mole % water. The low relative humidity environment is about 25% RH or less; and preferably, about 20% or less.

Alternatively, particles having an EDR of about 20% or less can be formulated by serial exposure to an acetone/water-containing atmosphere, and to an ethanol/water-containing atmosphere. That method involves: (a) creating particles consisting essentially of estradiol and cholesterol in about a 1:1 molar ratio wherein either or both are in an amorphous or polymorphic form; (b) exposing said particles to an atmosphere saturated with acetone and water; (c) repeating step (b) at least once, and preferably twice; (d) exposing said particles to an atmosphere saturated with ethanol and water; (e) drying the particles; and (f) recovering said particles; wherein the estradiol dissolution rate from the recovered particles in aqueous solution is less than about 20% (by weight) over 24 hours.

In preferred embodiments, particles are exposed to vapors of an acetone/water mixture for about two to about five consecutive stages of at least about 12 hours at about 20°-40° C. Preferably, the acetone/water stage is conducted in three consecutive stages over about 24 hours at about 30° C.

The relative concentration of the acetone/water mixture is as described above; and the ethanol/water mixture is a relative concentration of about 95 mole % to about 99 mole % ethanol; and about 5 mole % to about 1 mole % water. The particles can be dried at about 40° to about 50° C., preferably about 45° C., for about 24 hours or more, and preferably about 36 hours. The drying stages described here and above can be conducted under vacuum or in air.

More preferably, the alternative method involves: creating particles consisting essentially of estradiol and cholesterol in about a 1:1 molar ratio wherein either or both are in an amorphous or polymorphic form; exposing said particles to an atmosphere saturated with acetone and water at about 30° C. for three consecutive stages of about 24 hours; exposing said particles to an atmosphere saturated with ethanol and water for about two hours at about 30° C.; drying the particles at about 45° C. for about 42 hours; and recovering said particles; wherein the estradiol dissolution rate from the recovered particles in aqueous solution is less than about 20% (by weight) over 24 hours.

The methods of the present invention afford means for fabricating microspheres of estradiol and cholesterol having an EDR less than about 20% (by weight). Preferred embodiments have an EDR of about 15% or less, and more preferably about 6% or less. The estradiol of the microspheres of the present invention is in a hemicrystalline or composite form where about 50-60% is amorphous and about 40-50% is crystalline. Preferred embodiments are those wherein the estradiol is about 55% is amorphous and about 45% is crystalline.

The low EDR estradiol/cholesterol particles of the foregoing methods can be combined with progesterone to make low dose estradiol formulations that can be administered monthly or less often. For example, the invention affords a pharmaceutical formulation comprising about 5 to about 15 mg 17-β-estradiol admixed with cholesterol in about a 1:1 molar ratio, and about 300 to about 400 mg progesterone; wherein the weight ratio of 17-β-estradiol to progesterone is about 1:40, the 17-β-estradiol consists of a hemicrystalline form that is about 50-60% amorphous and about 40-50% crystalline, and the EDR of the formulation is about 20% or less. The pharmaceutical formulation can be prepared of particles of estradiol/cholesterol in combination with particles of a progestin, preferably progesterone. The particles are preferably microspheres. The particles can further include additives and excipients, such as lubricants, buffers, stabilizers, and the like. Additionally, the particles can be suspended in a carrier for parenteral administration. Those formulations have a contraceptive effect and can be used effectively in hormone replacement regimens involving parenteral administration once a month or even every other month. Preferably, the formulation is administered by intramuscular injection.

Without further description, it is believed that one of ordinary skill in the art can, using the preceding description and the following illustrative examples, make and use the formulations of the present invention and practice the claimed methods. The following working examples therefore, illustrate preferred embodiments and methods for making and using the present invention, and are not to be construed as limiting in any way the remainder of the disclosure.

Example 1

Pharmacokinetic Study in Rabbits to Assess the Bioavailabilty of Different Combinations of Progesterone Microspheres & Estradiol Microspheres and Microspheres at Different Ratios of Estradiol to Cholesterol This study is aimed at assessing the pharmacokinetic profile of test articles containing Progesterone (P) and 17-β-Estradiol (E). A prospective and comparative study was conducted in New Zealand male rabbits. Test articles consisted of aqueous suspensions using the aqueous vehicle described above of microspheres of progesterone+microspheres of estradiol (E) or estradiol cholesterol (EC), manufactured by following the process described in U.S. Pat. No. 5,360,616 and crystallized according to U.S. Pat. No. 6,528,094 B1. Test articles evaluated are the following:

| Test Article | Composition |
|---|---|
| A | P Microspheres (ME) + E ME |
| B | P ME + (1:1) Estradiol Cholesterol ME |
| C | P ME + (2:1) Estradiol Cholesterol ME |
| D | P ME + (3:1) Estradiol Cholesterol ME |

The aqueous suspensions were administered in the form of intramuscular (IM) injections. Each rabbit received 133 mg of progesterone and 3 mg of estradiol. Blood samples were collected at time 0 (predose), 1, 2, 4 and 9 hours, and every day from day 2 to 14, and every other day from day 14 to 28. The resulting samples were assayed for progesterone and estradiol by radioimmunoassay (RIA).

From the plasma profiles, the following pharmacokinetic parameters were calculated: Area Under the Curve to infinite (AUC_INF), Area Under the Curve to the last sampling time (ABC0_t), Maximum plasma concentration ($C_{max}$), time to reach the $C_{max}$ ($T_{max}$), Half-life ($t_{1/2}$), Elimination Constant ($K_e$), and Mean Residence Time (MRT). These results were analyzed statistically aimed at assessing any possible difference among groups.

Regarding the comparison of the parameters calculated for Estradiol, although the analysis showed no evidence of any possible statistically significant differences (p<0.05) in these parameters among the groups, as shown in the following table, there are differences in the MRT among the groups since the MRT for (1:1) EC ME (Test Article B) was almost twice longer than for E Microspheres (Test Article A), as seen in the following table:

|  | TEST ARTICLE | | | |
| --- | --- | --- | --- | --- |
|  | A | B | C | D |
| MRT (days) | 4.56 ± 1.05 | 8.33 ± 2.61 | 5.01 ± 0.55 | 6.40 ± 2.27 |
| CV | 23.3 | 31.3 | 11 | 35.5 |
| n | 4 | 4 | 4 | 4 |

Regarding the comparison of the parameters calculated for Progesterone although variability was observed in the parameters calculated, no statistically significant difference ($p<0.05$) was found among groups.

Graphical Analysis:

Mean plasma profiles for Estradiol and Progesterone for the four test articles evaluated are shown in FIGS. 1 and 2. According to results for estradiol and progesterone, although the statistical analysis showed no evidence of difference between groups, the graphic analysis of plasma profiles (See FIG. 1) showed different behavior. This may be attributable to the small sample size.

Example 2

Comparative

Microspheres of a Mixture of 49% 17-β-estradiol and 51% Cholesterol

This comparative example is analogous to the fabrication of particles according to Example 7 of U.S. Pat. No. 6,528,094 B1, which is incorporated herein by reference (also referred to herein as "Crystallization Process A"). The estradiol/cholesterol microspheres can be combined with progesterone microspheres to produce the pharmaceutical formulation of Test Article B of Example 1, above.

The microspheres of this mixture were obtained by melting together the components and, as for the pure substances, sprayed into droplets and congealed into microspheres. The microspheres initially showed a high amorphous content.

When the microspheres were placed in a recipient of approximately 7 liters and exposed for 24 hours at 30° C. to the vapors of 8 mL of ethanol kept in a porous cellulose material, the initially amorphous microspheres crystallized completely in the presence of the vapors.

The microspheres were dried at 60° C. in a vacuum for 24 hours, and residual ethanol present in the microspheres was less than 0.01%.

To evaluate the stability of the microspheres, non-crystallized microspheres (melt-congealed only) and microspheres according to the present invention were separately placed in aqueous solution at 40° C., and observed by optical microscopy after 82 days. As observed by optical microscopy, the microspheres crystallized according to the present invention remained stable over time when placed in water, whereas the non-crystallized microspheres did not.

The resulting crystallized microspheres were morphologically stable for 82 days when placed in a solution of 0.01% Polysorbate 80 in USP purified water at 40° C., or for 14 days when they were injected intramuscularly into rabbits.

Figure 3B:
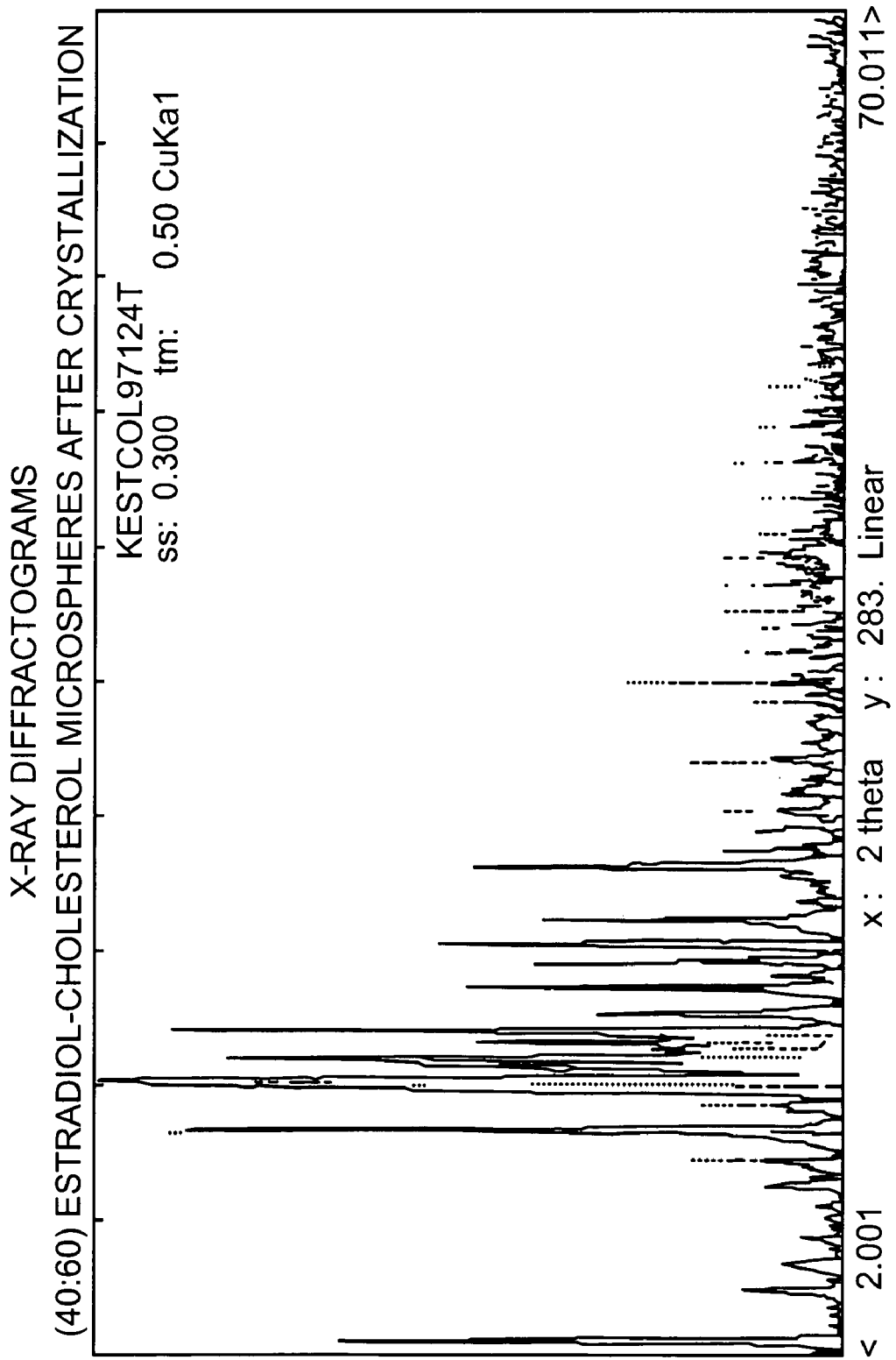
FIG. 3B: An X-ray diffractogram of (40:60) estradiol-cholesterol microspheres after crystallization.
Figure 6:
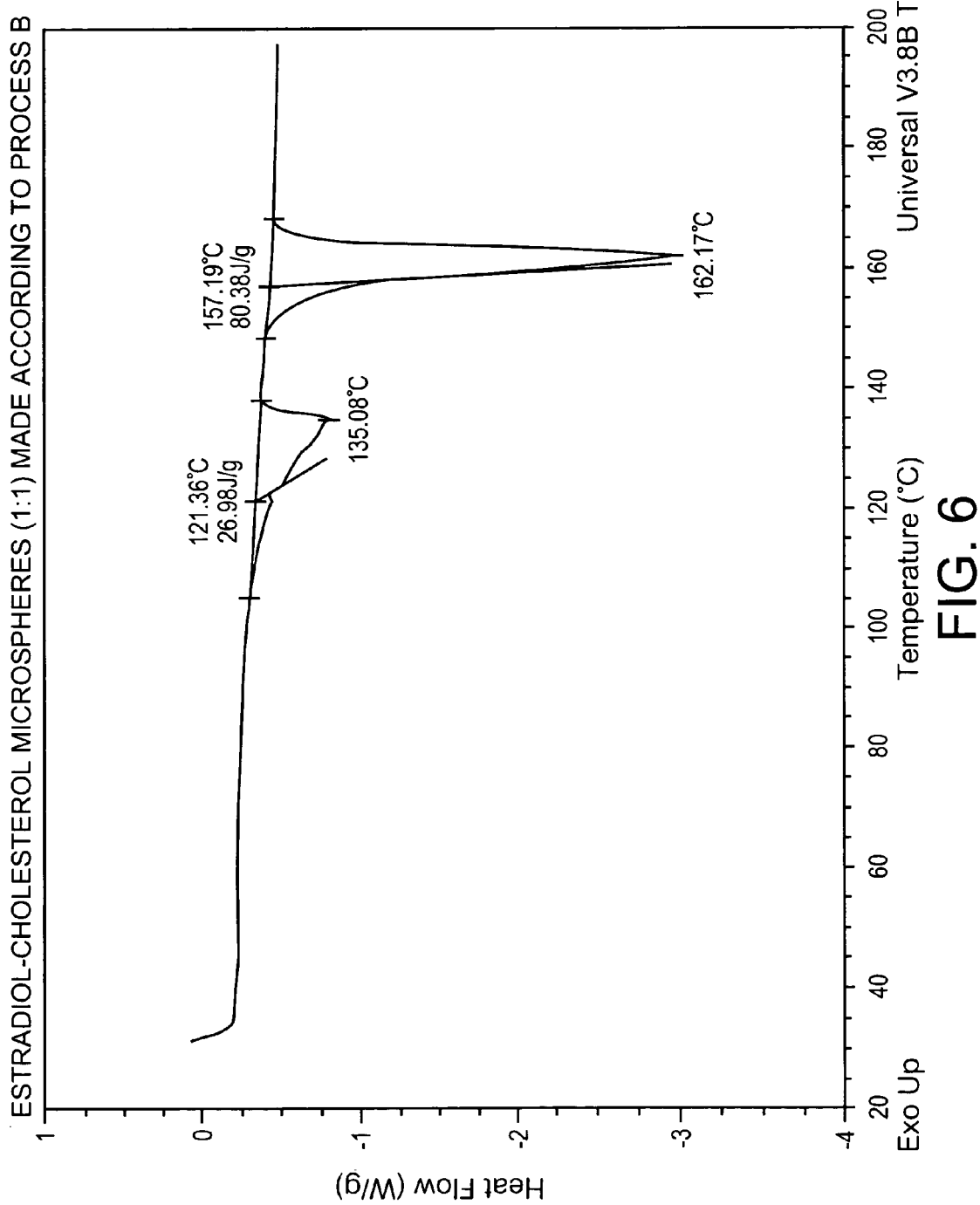
FIG. 6: DSC of (1:1) estradiol-cholesterol miscrospheres made according to Process B.
Figure 7:
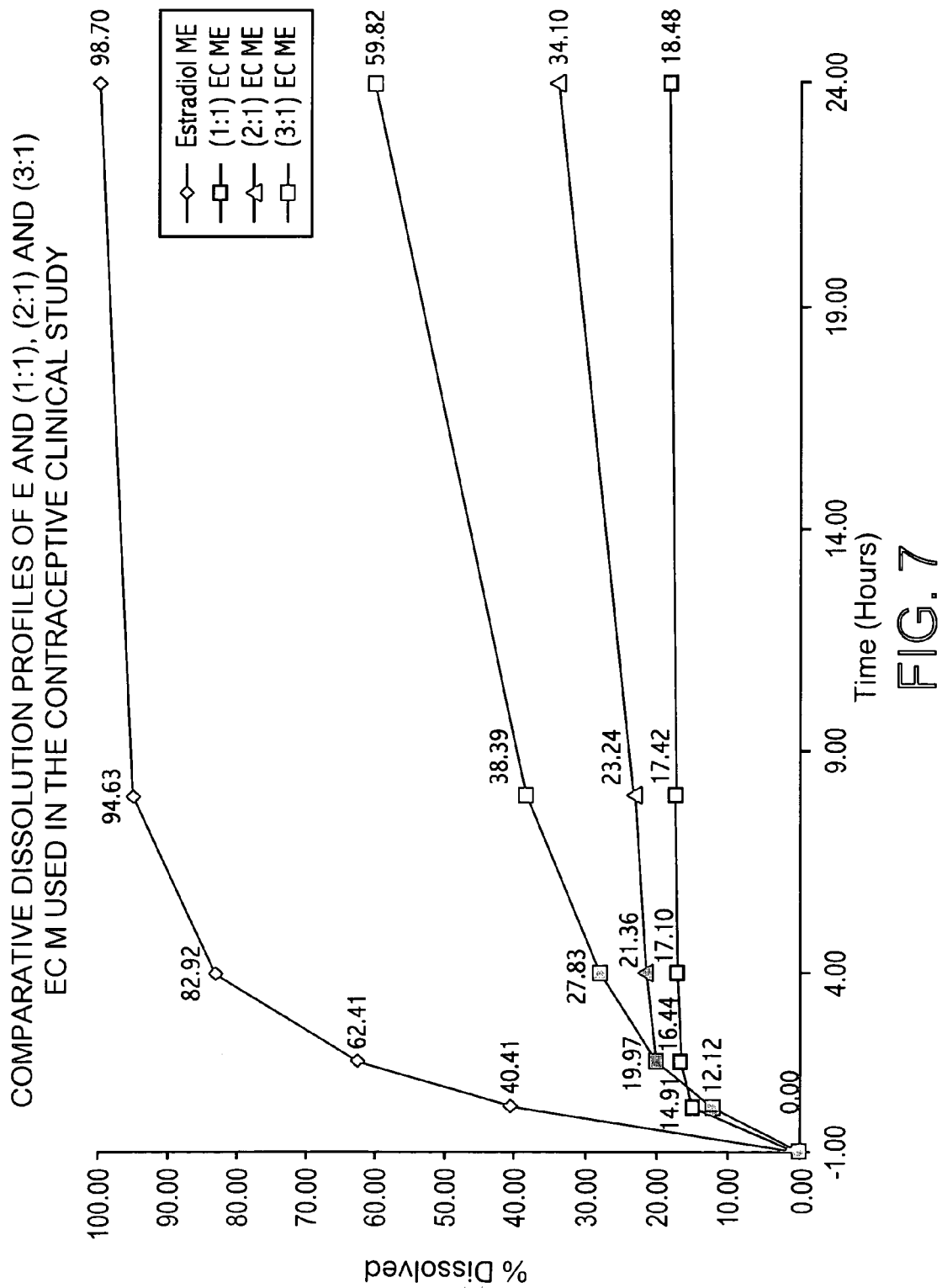
FIG. 7: Comparative dissolution profiles of microspheres of estradiol (E); and estradiol-cholesterol (1:1), (1:2), and (1:3) as used in the contraceptive clinical study and made according to Crystallization Process B.
Figure 8:
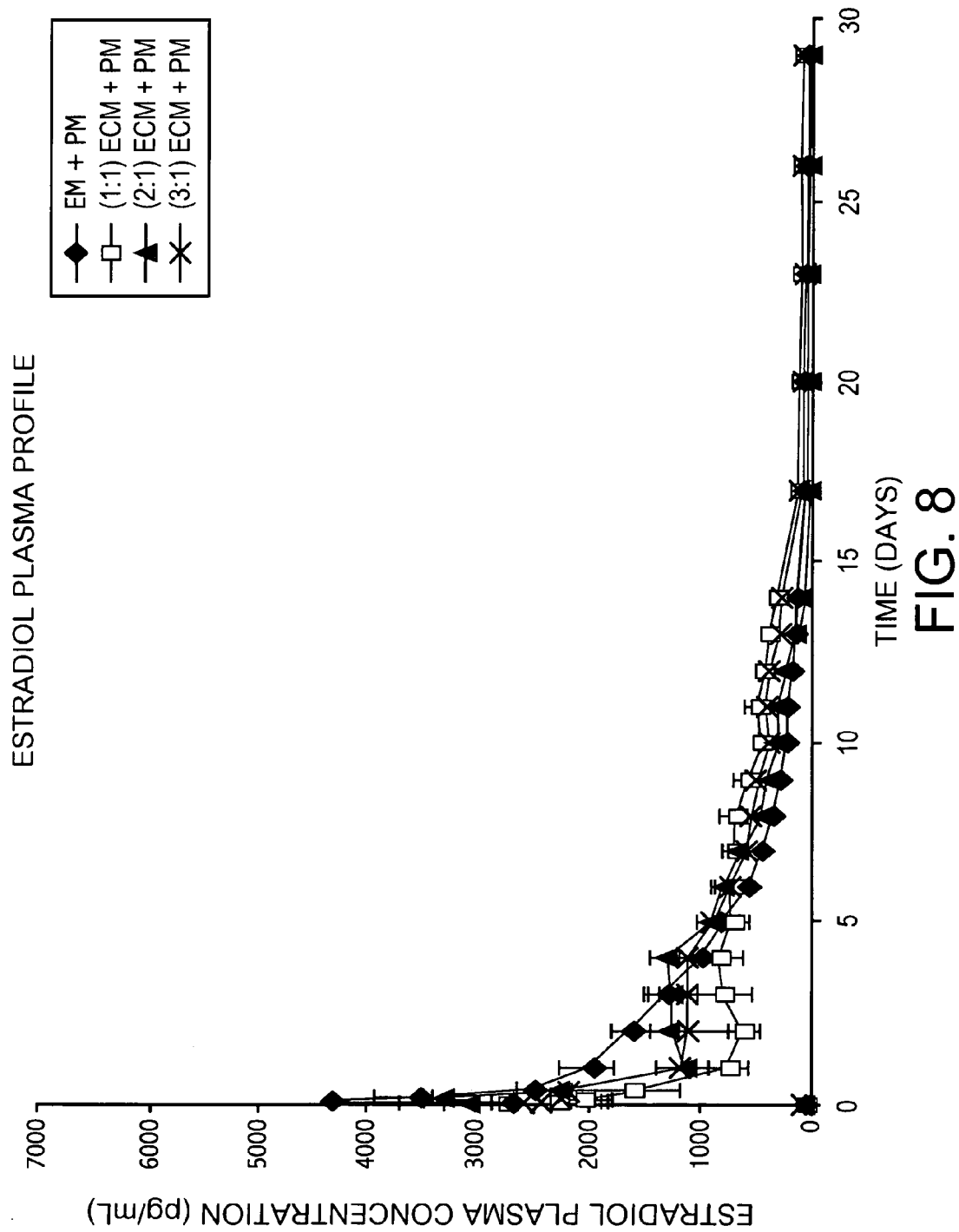
FIG. 8: Estradiol plasma profile as a function of time for microspheres of estradiol (E) and estradiol-cholesterol (1:1), (1:2), and (1:3) made according to Crystallization Process B.
Figure 9:
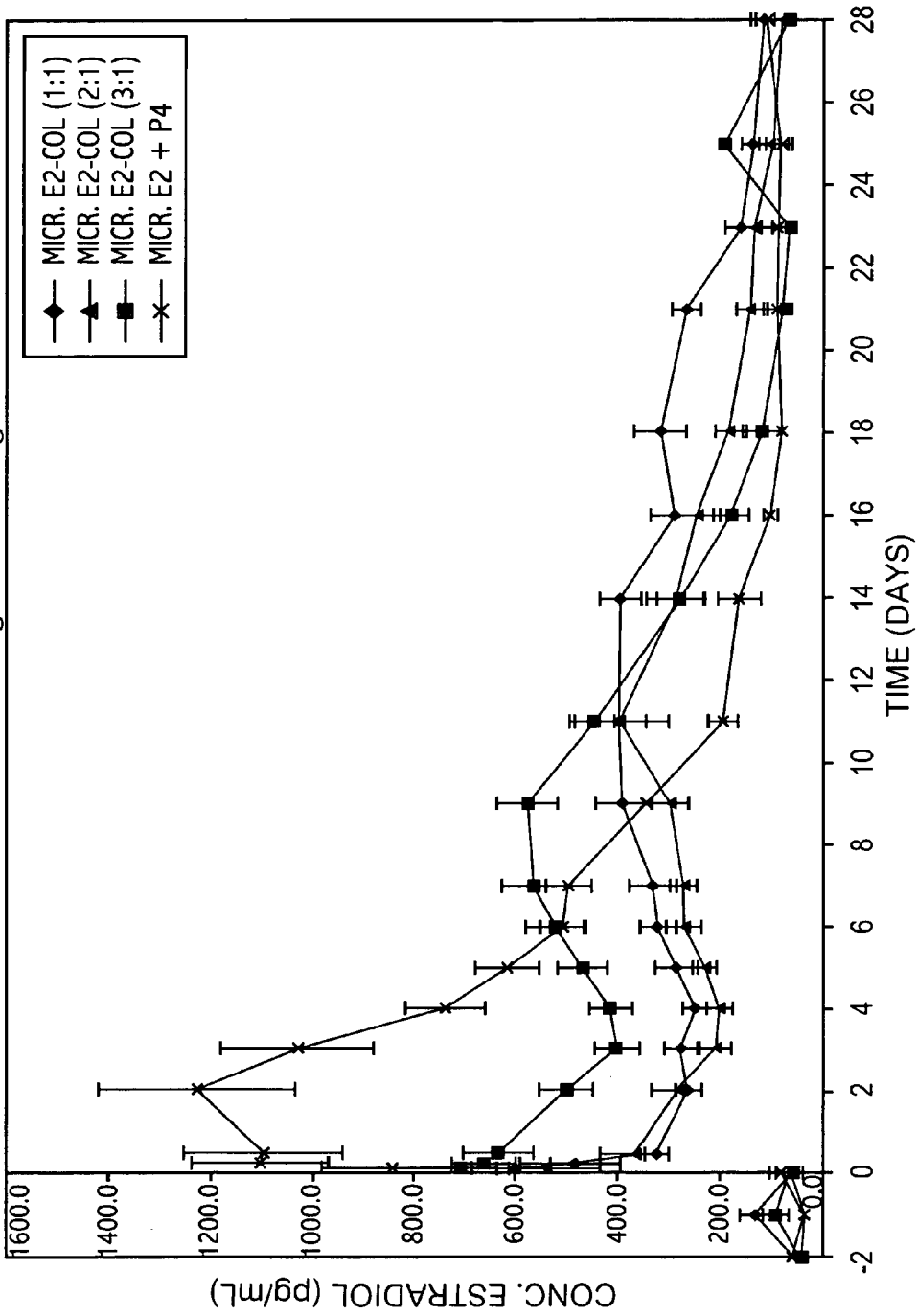
FIG. 9: Estradiol plasma profile as a function of time for microspheres of estradiol (E) and estradiol-cholesterol (1:1), (1:2), and (1:3); dose estradiol 9 mg and progesterone 400 mg; and made according to Crystallization Process B.
Figure 10:
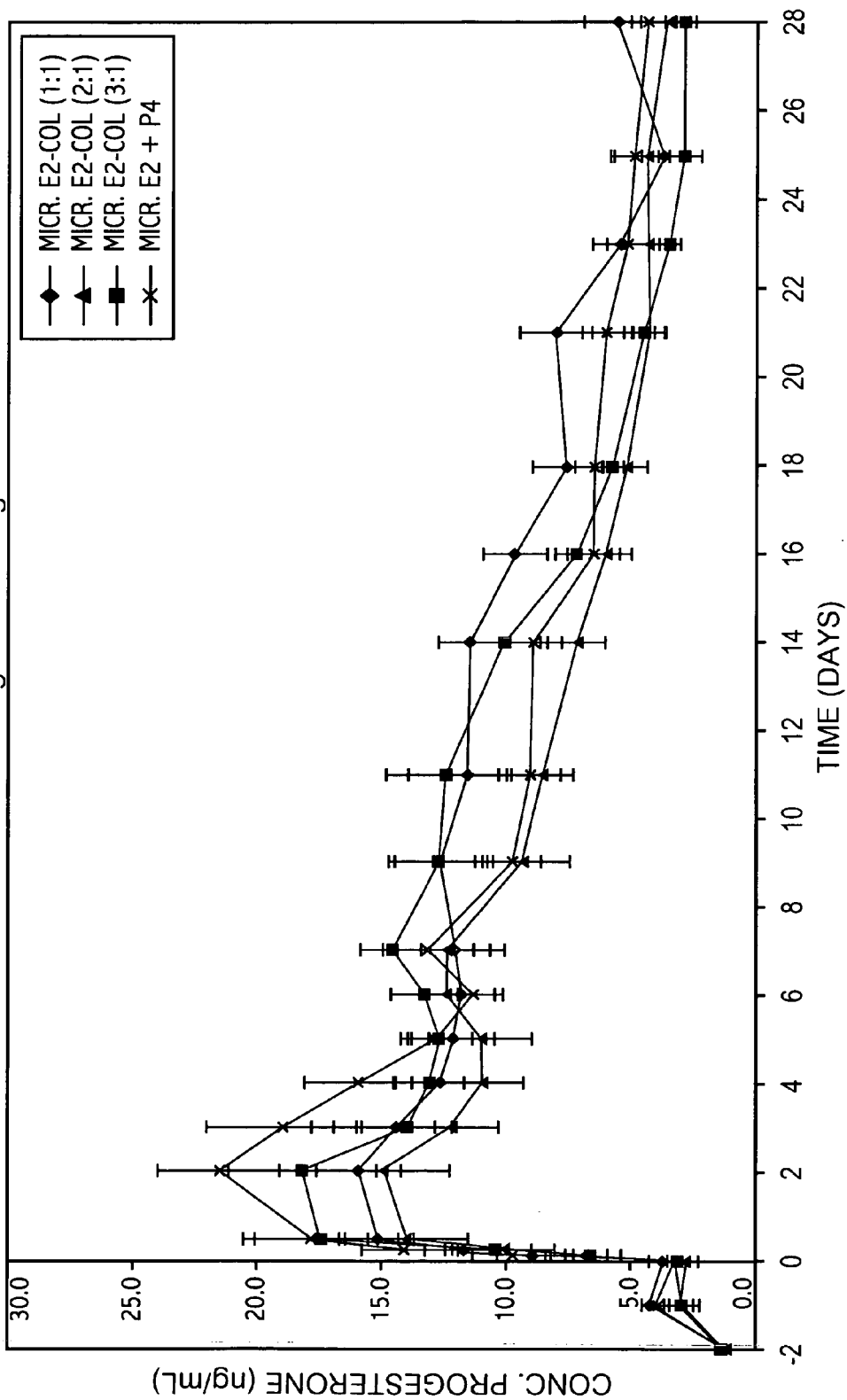
FIG. 10: Progesterone plasma profile as a function of time for microspheres of estradiol (E) and estradiol-cholesterol (1:1), (1:2), and (1:3); dose estradiol 9 mg and progesterone 400 mg; and made according to Crystallization Process B.
Figure 11:
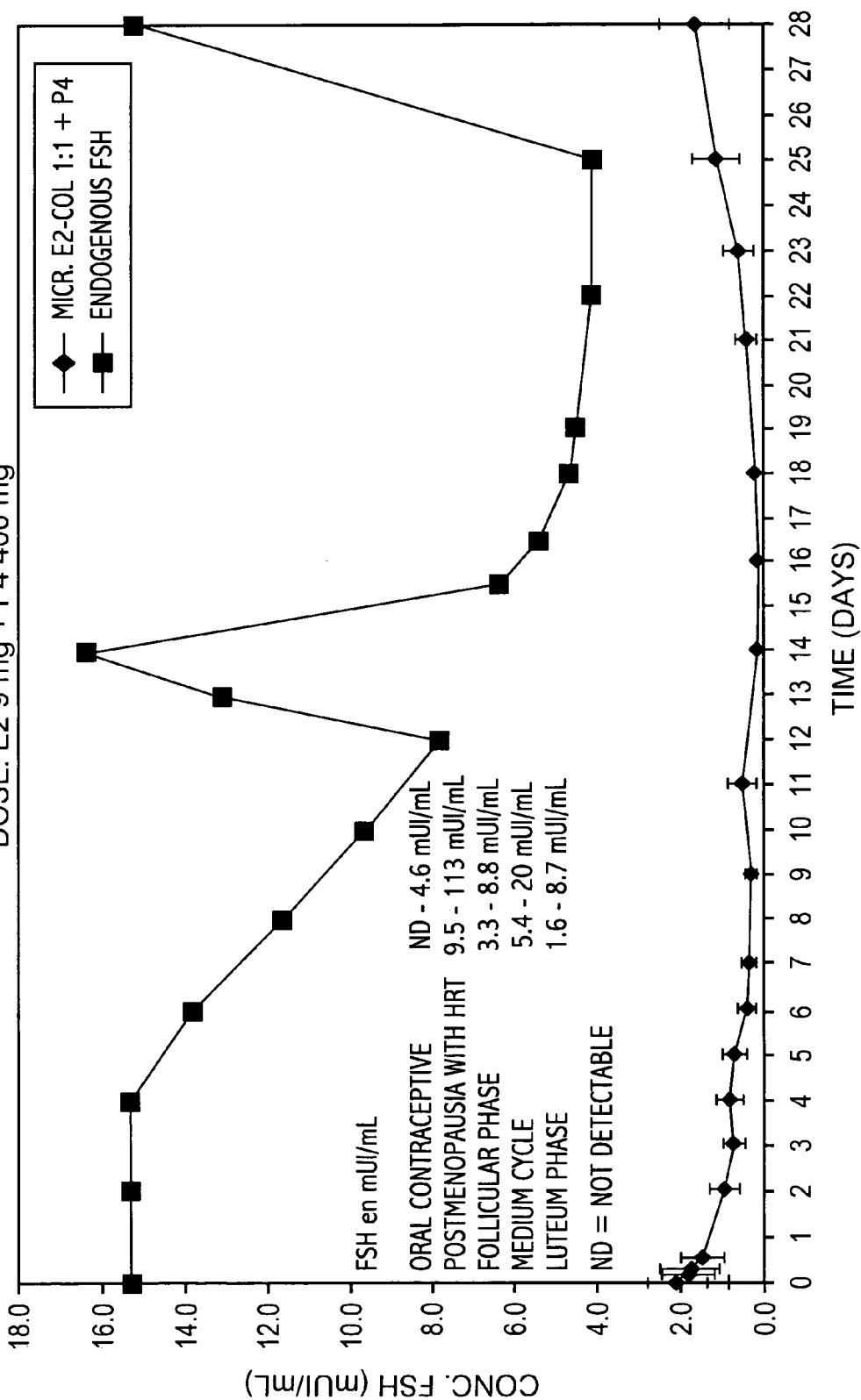
FIG. 11: FSH plasma profile as a function of time for microspheres of estradiol-cholesterol (1:1) and progesterone; dose, estradiol 9 mg and progesterone 400 mg; and made according to Crystallization Process B versus endogenous FSH.
Figure 12:
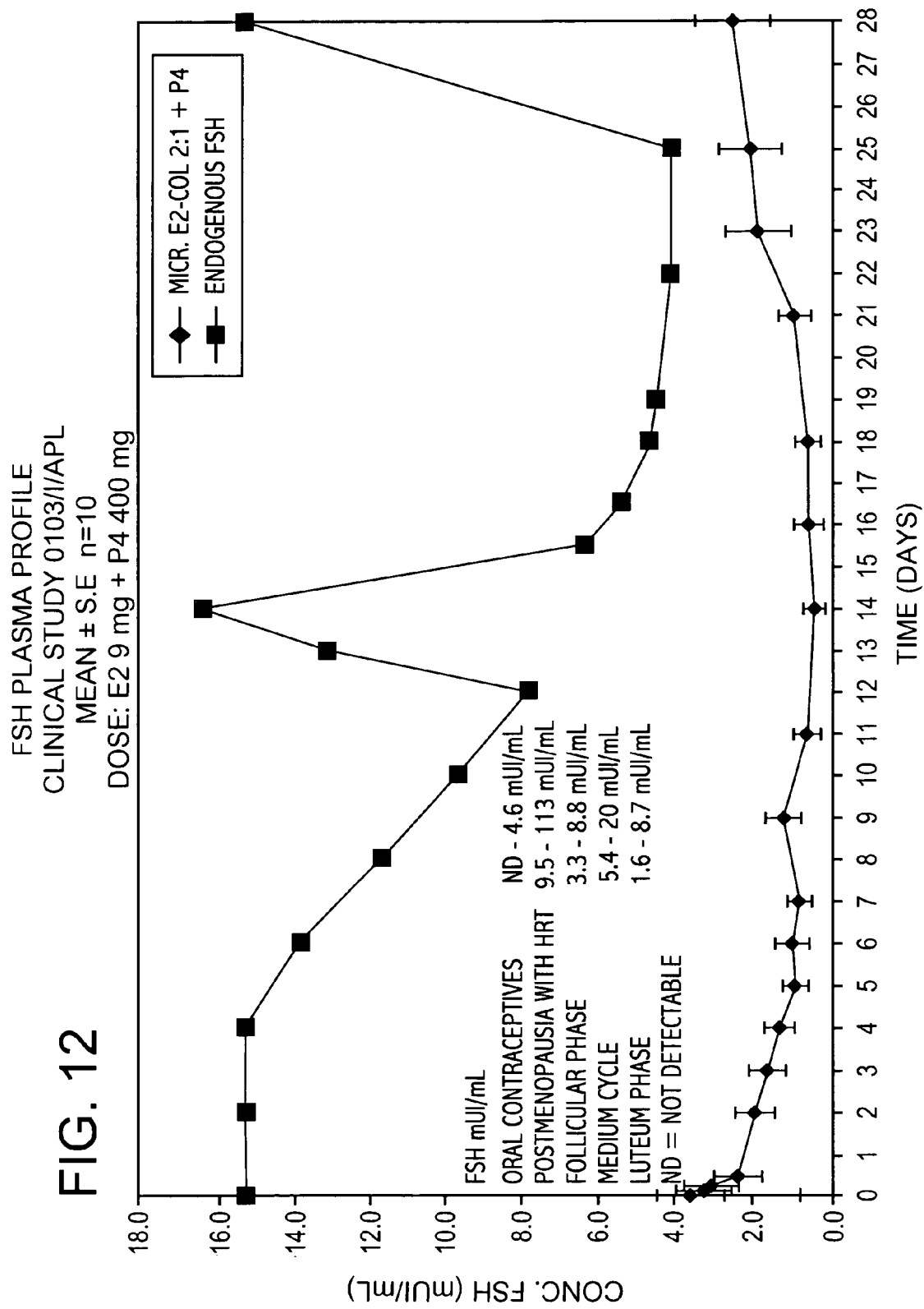
FIG. 12: FSH plasma profile as a function of time for microspheres of estradiol-cholesterol (2:1) and progesterone; dose, estradiol 9 mg and progesterone 400 mg; and made according to Crystallization Process B versus endogenous FSH.
Figure 13:
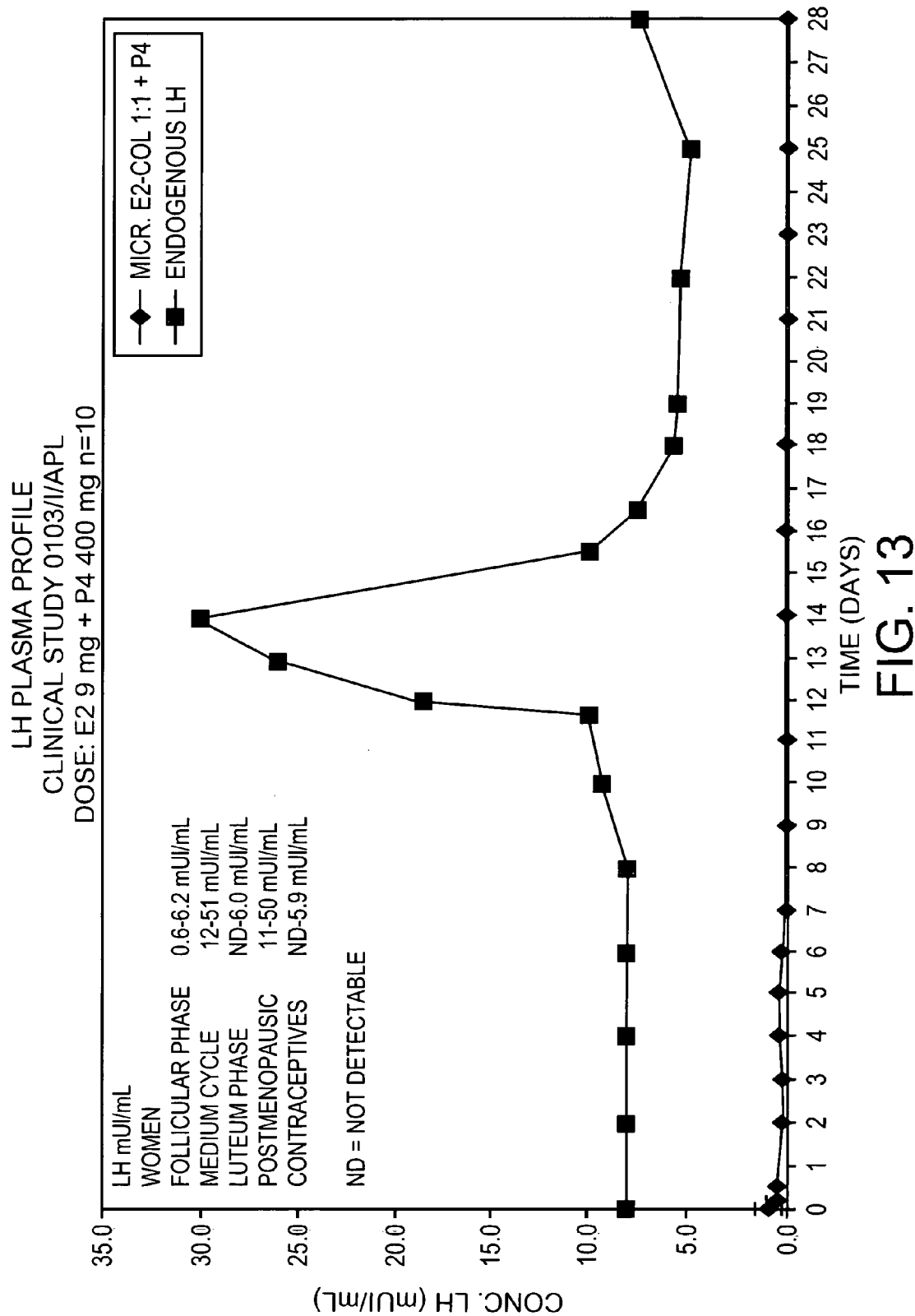
FIG. 13: Luteinizing Hormone plasma profile as a function of time for microspheres of estradiol-cholesterol (1:1) and progesterone; dose, estradiol 9 mg and progesterone 400 mg; and made according to Crystallization Process B versus endogenous LH.
Figure 14:
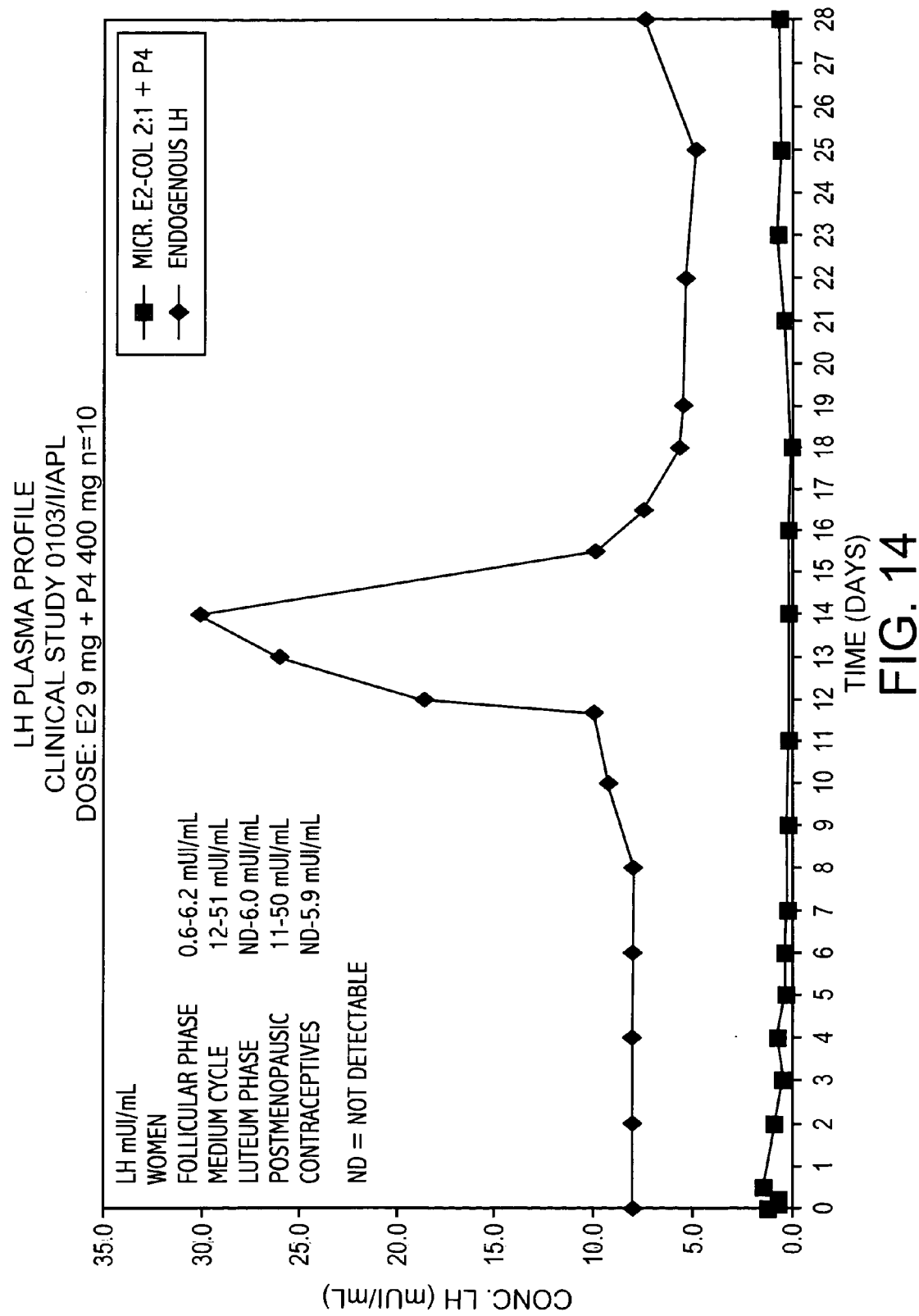
FIG. 14: Luteinizing Hormone plasma profile as a function of time for microspheres of estradiol-cholesterol (2:1) and progesterone; dose, estradiol 9 mg and progesterone 400 mg; and made according to Crystallization Process B versus endogenous LH.
Figure 15:
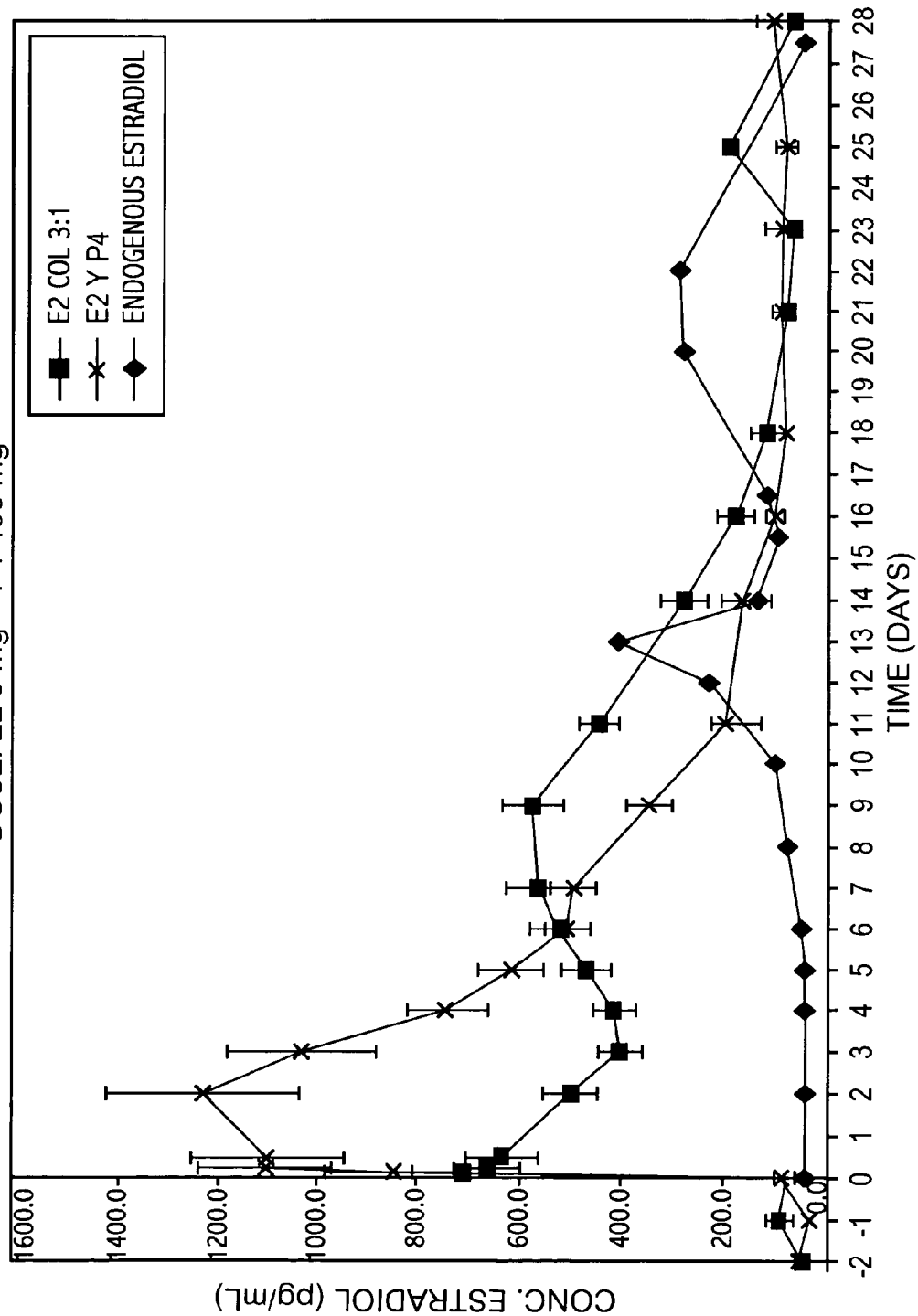
FIG. 15: Estradiol plasma profile as a function of time for microspheres of estradiol-cholesterol (3:1) and progesterone, and estradiol and progesterone; dose, estradiol 9 mg and progesterone 400 mg; and made according to Crystallization Process B versus endogenous estradiol.
Figure 16:
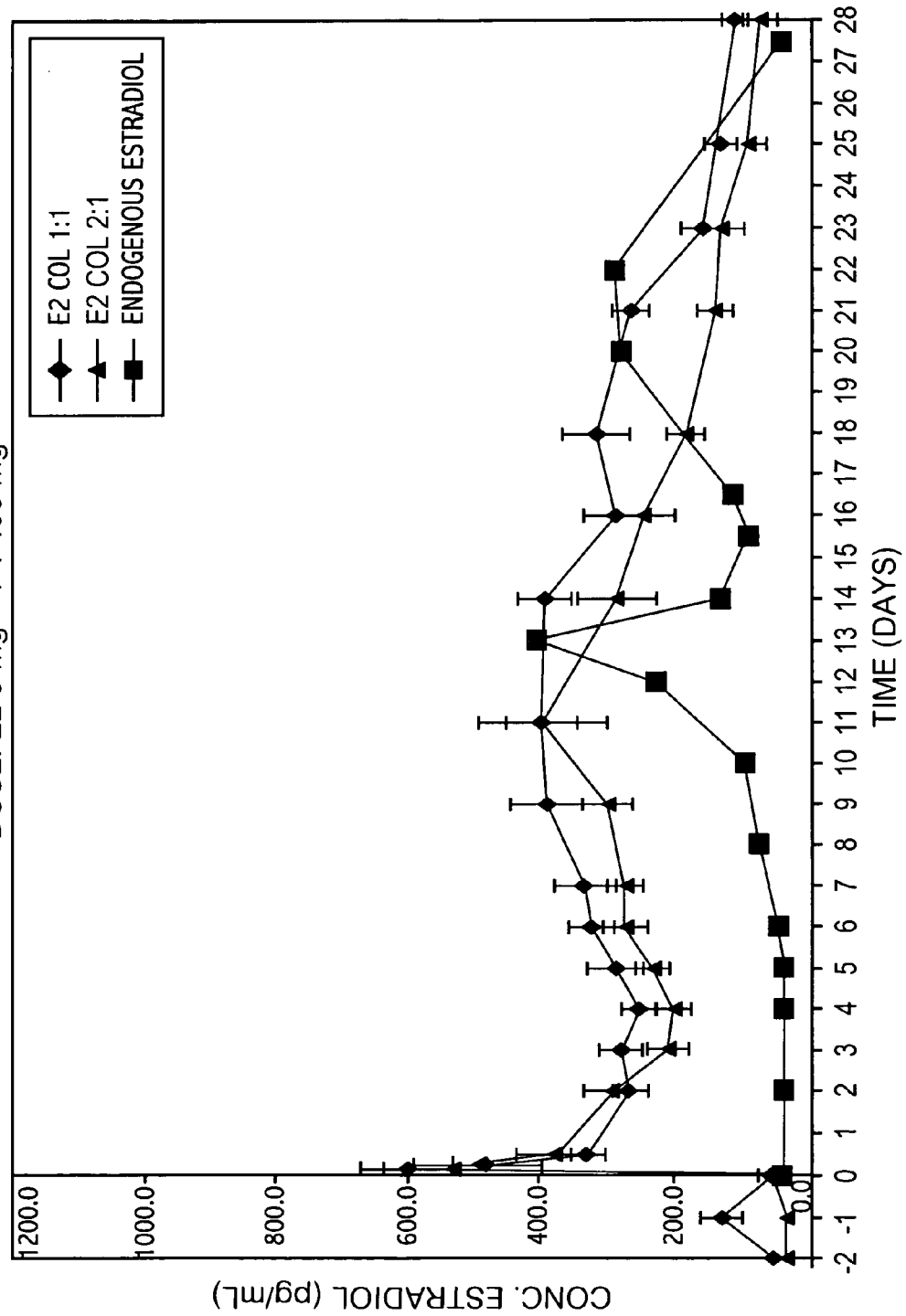
FIG. 16: Estradiol plasma profile as a function of time for microspheres of estradiol-cholesterol (1:1) and progesterone, and estradiol-cholesterol (2:1) and progesterone; dose, estradiol 9 mg and progesterone 400 mg; and made according to Crystallization Process B versus endogenous estradiol.
Figure 17:
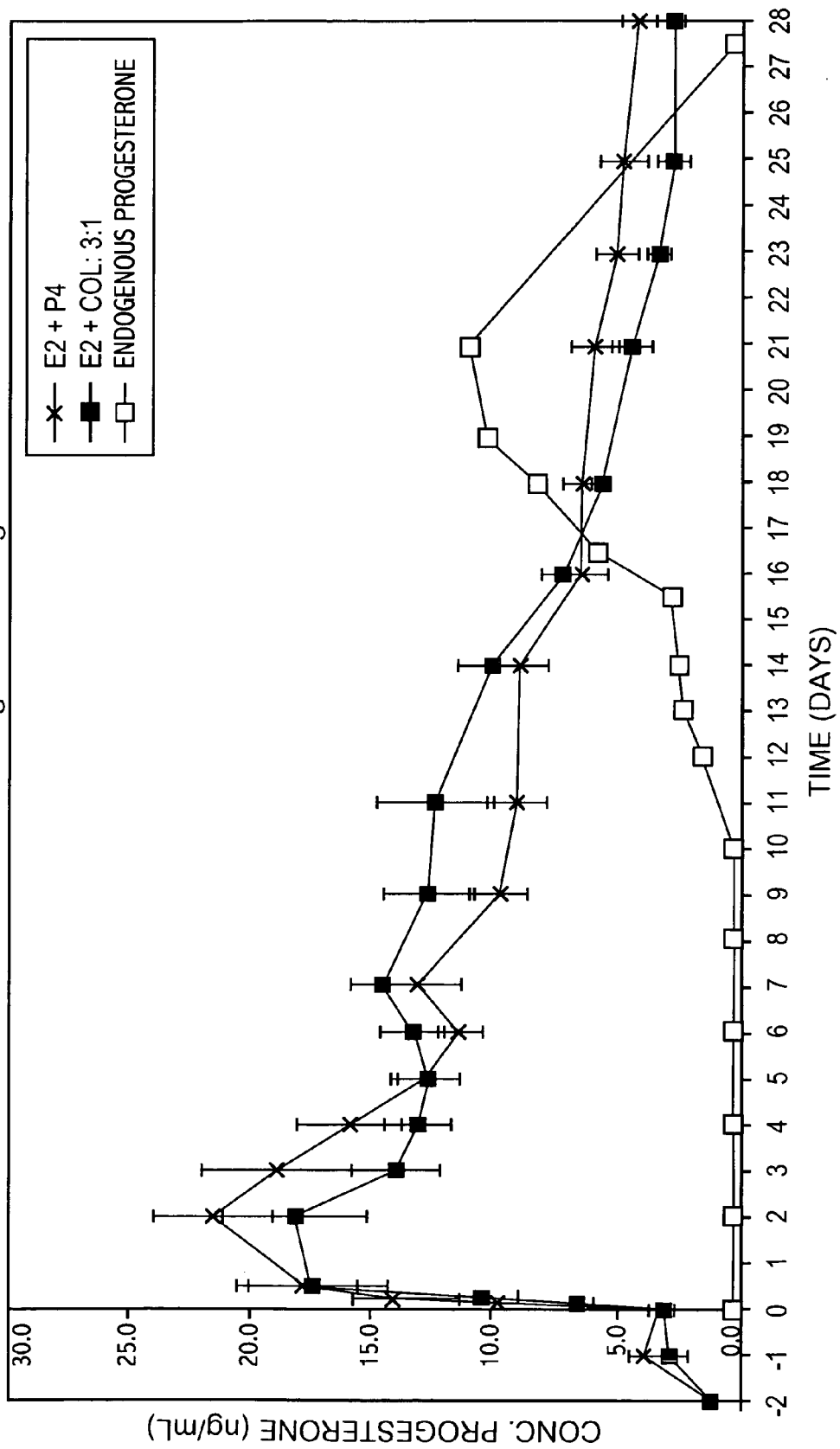
FIG. 17: Progesterone plasma profile as a function of time for microspheres of estradiol and progesterone, and estradiol-cholesterol (3:1) and progesterone; dose, estradiol 9 mg and progesterone 400 mg; and made according to Crystallization Process B versus endogenous progesterone.
Figure 18:
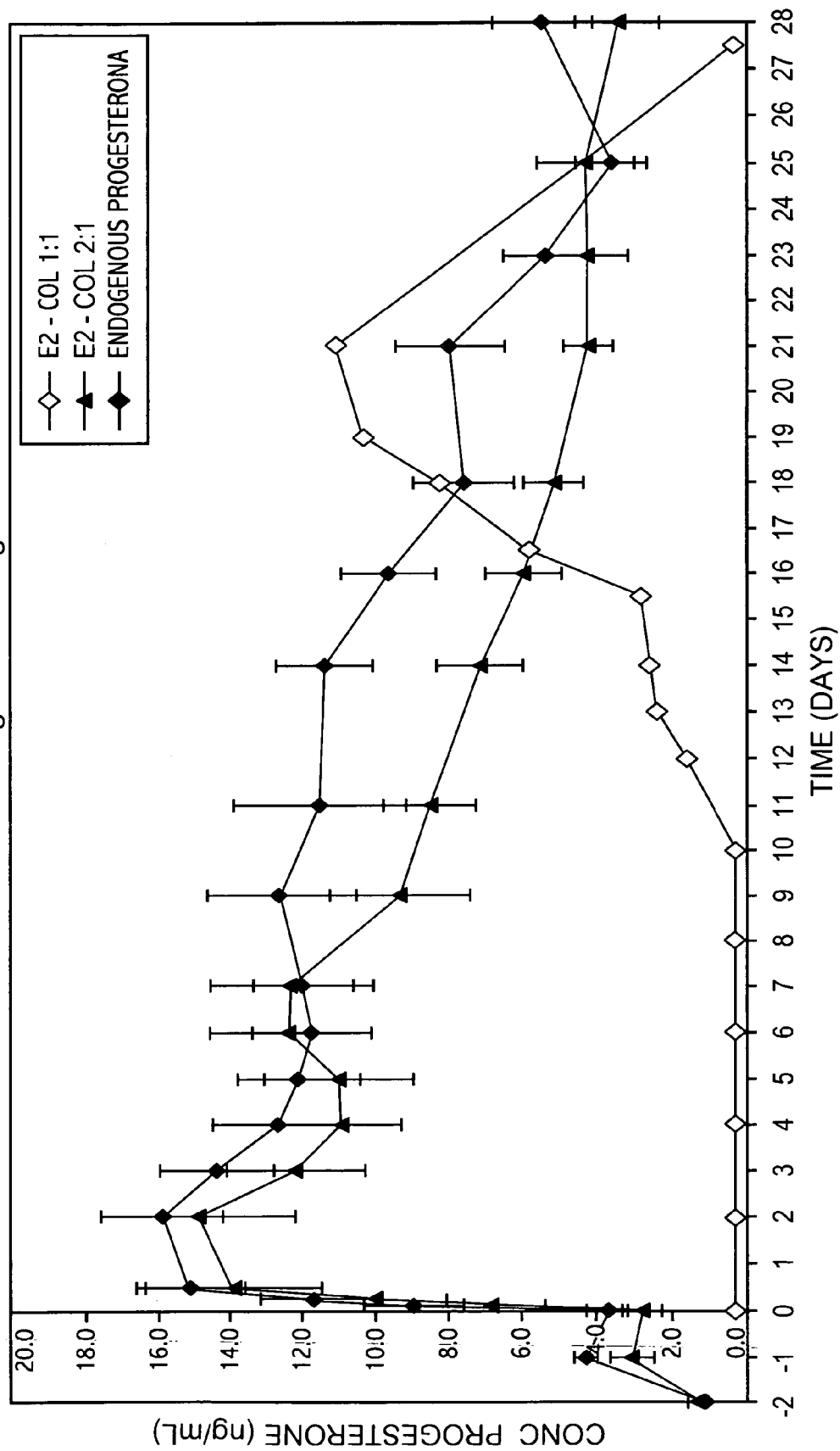
FIG. 18: Progesterone plasma profile as a function of time for microspheres of estradiol-cholesterol (1:1) and progesterone, and estradiol-cholesterol (2:1) and progesterone; dose, estradiol 9 mg and progesterone 400 mg; and made according to Crystallization Process B versus endogenous progesterone.

FIG. 3 shows the X-ray diffractogram of the EC (40:60) Microspheres before and after crystallization; and FIG. 4 shows the corresponding dissolution profile (i.e., 74% of estradiol dissolved at 24 hours in an aqueous solution of 0.3% Tween 80®).

Example 3

Modified Crystallization Process for EC ME Presenting 20% Dissolution Over 24 Hours ("Crystallization Process B")

Estradiol-cholesterol (1:1) microspheres were fabricated as in Example 2, above. The microspheres, having a high amorphous content, were exposed to vapors of acetone and water (95 mole %️ acetone: 5 mole % water) for three consecutive 24 hour stages at 30° C. Between stages, hermetic containers are opened and the contents dried with air, residual solvent is removed and then the estradiol microspheres are submitted to the next vapor-exposure stage.

The particles were then heated (desiccated) at 45° C. for 42 hours under vacuum (about 12.2 in. Hg).

The resulting particles produced an average EDR of about 20%. See FIG. 5.

Example 4

Crystallization Process for Ultralow Dissolution of Estradiol-Cholesterol Microspheres ("Crystallization Process C")

Estradiol-cholesterol microspheres were fabricated according to the process of Example 2. The particles were stored under low relative humidity for 24 hours. The particles were then exposed to vapors of acetone and water (72 mole % acetone/28 mole % water) for 72 hours at 60° C. The particles were then heated (for desiccation) at 45° C. for 42 hours.

The resulting particles had an average of about 5% dissolution of estradiol over 24 hours in an aqueous solution of 0.3% polyoxyethylenesorbitan monooleate (Tween 80®) at standard temperature and pressure.

Figure 19:
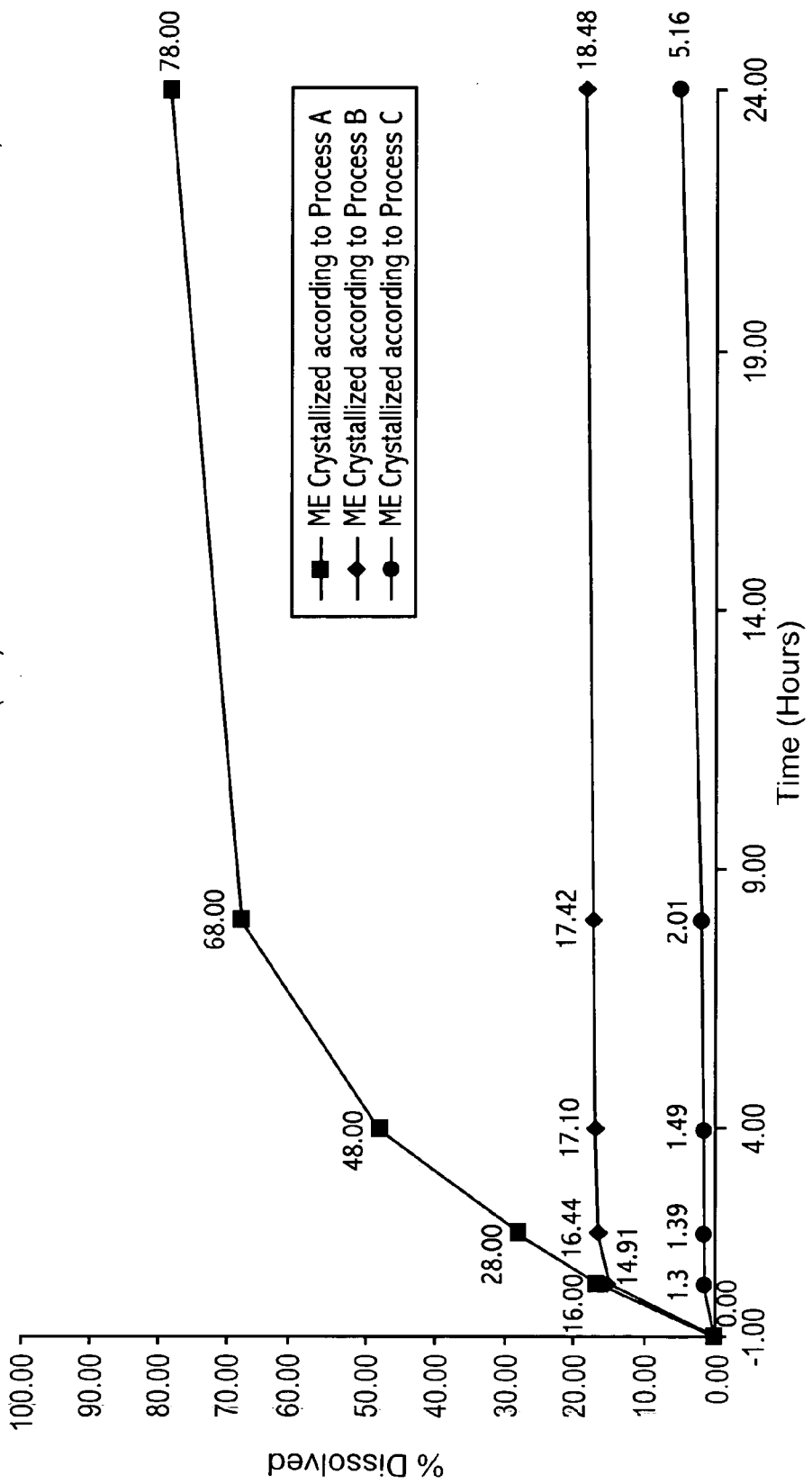
FIG. 19: Comparative dissolution profiles of (1:1) estradiol-cholesterol microspheres as prepared by Crystallization Processes A, B, and C.

FIG. 19 illustrates the dissolution profile of the particles of this Example compared to those resulting from the methods of Examples 2 and 3.

Figure 20:
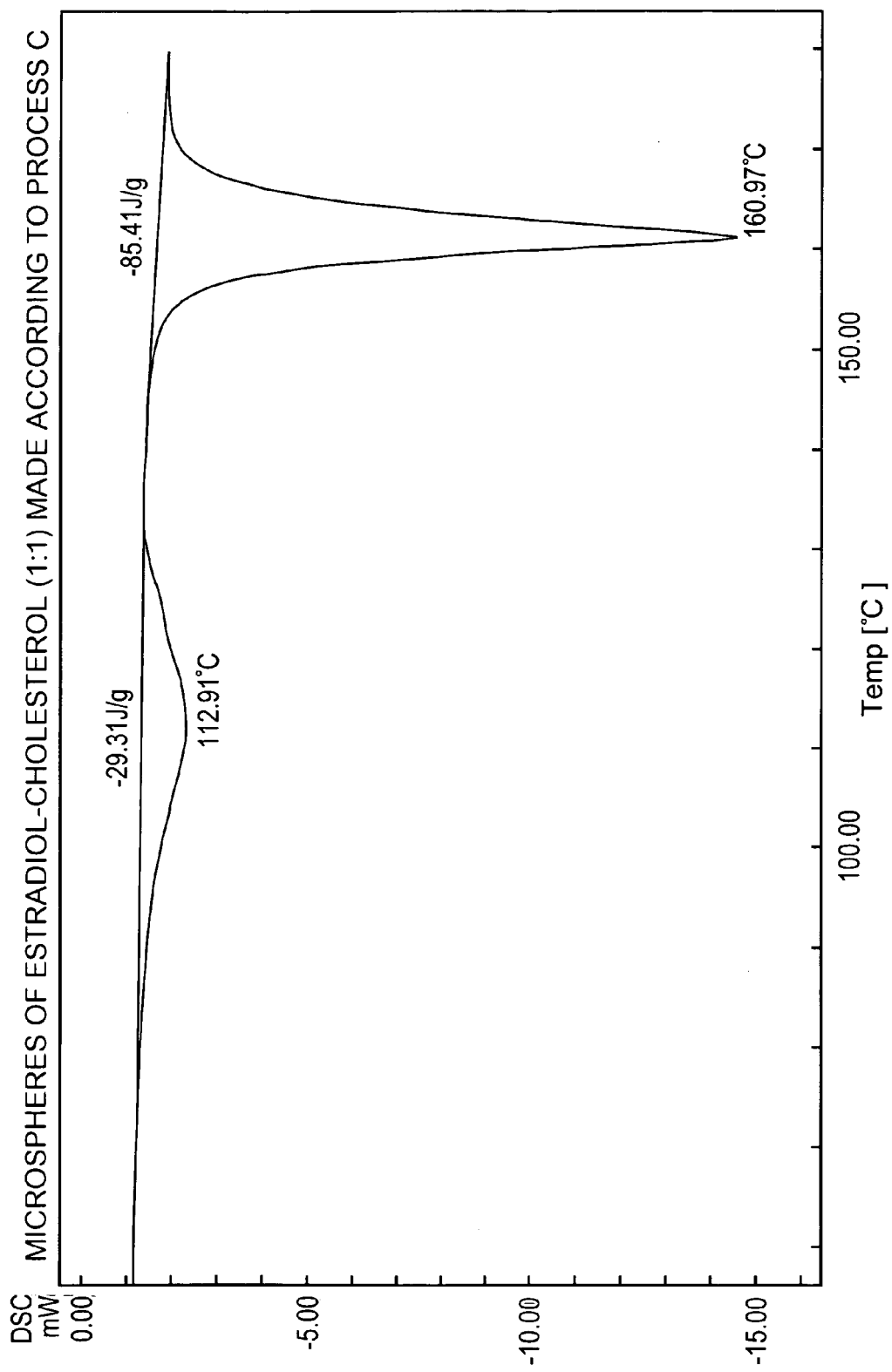
FIG. 20: DSC of microspheres of estradiol-cholesterol (1:1) made according to Process C.

FIG. 20 shows the DSC profile of the particles resulting from this Example.

FIGS. 21 and 22 are X-ray diffractograms of the particles resulting from Example 4.

While the present invention has been described with reference to specific embodiments, this application is intended to cover those various changes and substitutions that may be made by those of ordinary skill in the art without departing from the spirit and scope of the appended claims.

What is claimed is:

1. A method for effecting simultaneous contraception and hormone replacement therapy in a female mammal comprising administering to said mammal a pharmaceutical formulation comprising particles of 17-β-estradiol and cholesterol in about a 1:1 molar ratio, and particles of progesterone; wherein the weight ratio of 17-β-estradiol to progesterone is about 1:40, and wherein the 17-β-estradiol is about 50-60% amorphous and about 40-50% crystalline.

2. The method of claim 1, wherein the pharmaceutical formulation has an EDR of about 10% or less.

3. The method of claim 1, wherein the pharmaceutical formulation has an EDR of about 6% or less.

4. The method of claim 1, wherein the pharmaceutical formulation comprises about 5 to about 15 mg of 17-β-estradiol and about 300 to about 500 mg progesterone.

5. The method of claim 1, wherein the 17-β-estradiol of the pharmaceutical formulation is about 55% amorphous and about 45% crystalline.

6. The method of claim 1, wherein the administration is by intramuscular injection.

7. The method of claim 1, wherein the formulation is administered about once a month or less frequently.

8. The method of claim 1, wherein the formulation is administered about once every other month.

9. The method of claim 1, wherein the mammal is a human.

10. A method for simultaneous contraception and hormone-replacement, the method comprising administering to a mammal in need of such therapy a pharmaceutical formulation comprising about 5 to about 15 mg 17-β-estradiol that is 50-60% amorphous and 40-50% crystalline, and about 300 to about 500 mg progesterone.

11. The method of claim 10, wherein the administration of the pharmaceutical formulation is repeated at about one month.

12. The method of claim 10, wherein the pharmaceutical formulation is administered by intramuscular injection.

13. The method of claim 10, wherein the mammal is a human.

14. The method of claim 10, wherein the formulation comprises an aqueous suspension of microspheres consisting essentially of 17-β-estradiol and cholesterol, and microspheres consisting essentially of progesterone.

15. The method of claim 14, wherein the 17-β-estradiol and cholesterol are in a molar ratio of about 1:1, and the weight ratio of 17-β-estradiol to progesterone is about 9:400.

16. A method for simultaneous contraception and hormone-replacement, the method comprising administering to a mammal a pharmaceutical formulation comprising particles consisting essentially of 17-β-estradiol and cholesterol, and particles consisting essentially of progesterone; and wherein the 17-β-estradiol and progesterone are in a weight ratio of about 1:40, and wherein the 17-β-estradiol is 50-60% amorphous.

17. The method of claim 16, wherein the administration of the pharmaceutical formulation is repeated after about one complete menstrual cycle of the subject.

18. The method of claim 16, wherein the pharmaceutical formulation is administered by intramuscular injection.

19. The method of claim 16, wherein the mammal is a human and the administration of the formulation is repeated at about one month.

20. The method of claim 16, wherein the particles are microspheres having a diameter of between about 35 μm to about 75 μm.

* * * * *